(12) United States Patent
Sorensen et al.

(10) Patent No.: US 6,572,843 B1
(45) Date of Patent: Jun. 3, 2003

(54) METHOD FOR TREATING HAIR

(75) Inventors: Niels Henrik Sorensen, Skaevinge (DK); Jason Patrick McDevitt, Alpharetta, GA (US)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/523,298

(22) Filed: Mar. 10, 2000

Related U.S. Application Data

(63) Continuation-in-part of application No. 09/451,807, filed on Dec. 1, 1999, now abandoned, which is a continuation of application No. PCT/DK99/00674, filed on Dec. 1, 1999, and a continuation-in-part of application No. 09/203,075, filed on Dec. 1, 1998.

(51) Int. Cl.[7] .............................................. A61K 7/135
(52) U.S. Cl. .............................. 424/62; 424/60; 424/62; 424/63; 424/70.2; 424/70.4; 424/70.6; 424/613; 424/616; 424/615; 424/693; 514/731; 514/728; 435/28; 435/189; 435/192; 8/401; 8/406; 8/416; 8/421; 8/649
(58) Field of Search .......................... 8/401, 406, 416, 8/421, 649; 424/60, 62, 63, 70.2, 70.4, 70.6, 613, 616, 615, 693; 514/731, 728; 435/189, 28, 192

(56) References Cited

U.S. PATENT DOCUMENTS

| | | | |
|---|---|---|---|
| 3,251,742 A | 5/1966 | Soloway | 167/88 |
| 3,957,424 A | 5/1976 | Zeffren et al. | 8/10.2 |
| 4,961,925 A | 10/1990 | Tsujino et al. | 424/71 |
| 5,899,212 A * | 5/1999 | Sorensen et al. | 8/401 |
| 5,948,121 A | 9/1999 | Aaslyng et al. | |
| 6,036,729 A | 3/2000 | Barfoed et al. | |
| 6,238,658 B1 * | 5/2001 | Nguyen et al. | 424/70.2 |
| 6,261,325 B1 * | 7/2001 | De la Metrie et al. | 8/405 |

FOREIGN PATENT DOCUMENTS

| | | |
|---|---|---|
| EP | 0 328 816 A2 | 8/1989 |
| EP | 0 504 005 B1 | 9/1992 |
| EP | 0 548 620 A1 | 6/1993 |
| FR | 2 694 018 A1 | 1/1994 |
| WO | WO 96/10079 | 4/1996 |
| WO | WO 97/19998 | 6/1997 |
| WO | WO 97/19999 | 6/1997 |
| WO | WO 98/15257 | 4/1998 |
| WO | WO 99/58013 | 11/1999 |

OTHER PUBLICATIONS

Abstract of British Patent GB 1077758, Aug. 2, 1967.

* cited by examiner

*Primary Examiner*—Russell Travers
*Assistant Examiner*—Shahnam Sharareh
(74) *Attorney, Agent, or Firm*—Elias J. Lumbris

(57) ABSTRACT

A method for treating hair, combining permanent dyeing and straightening of hair, without significantly damaging the hair. According to the method of the present invention the hair is treated by chemically reducing covalent disulfide linkages in the hair, and contacting said hair with at least one oxidoreductase, at least one mediator, and at least one chemical oxidizing agent in an amount equivalent to 0.001–1% hydrogen peroxide calculated by weight of the dyeing formulation.

14 Claims, 1 Drawing Sheet

METHOD FOR TREATING HAIR

CROSS REFERENCE TO RELATED APPLICATIONS

This application is a continuation-in-part of application Ser. No. 09/451,807 filed on Dec. 1, 1991 now abandoned which is a continuation-in-part of application Ser. No. 09/203,075 filed on Dec. 1, 1998 and is a continuation and claims priority under 35 U.S.C. 120 of PCT/DK/99/00674 filed on Dec. 1, 1999, the contents of which are fully incorporated herein by reference.

FIELD OF THE INVENTION

The present invention relates to a method for dyeing hair that has been subjected to a chemical reduction step, more particularly, to a method for dyeing such hair by means of at least one oxidoreductase and at least one chemical oxidizing agent such as peroxide.

BACKGROUND OF THE INVENTION

Hair setting processes, including both permanent waving and straightening, are usually carried out at room temperature. The process typically includes at least two fundamental steps: i) reducing covalent disulfide linkages in the keratinous fibres of the hair, thereby rendering the hair deformable without elasticity, the hair typically being wetted by a solution containing a reducing agent and either rolled on curlers or mechanically straightened, and ii) rinsing and neutralization of the reducing agent, followed by re-establishment of a network of cross links in the keratinous fibres of the hair, either by air oxidation or by application of a so-called fixer (which usually contains an oxidizing agent), thereby rendering the curly or straightened shape "permanent".

For the purpose of breaking the disulfide cross links, a number of reducing agents can be used, including strong bases such as sodium hydroxide and guanidinium hydroxide, as well as weaker bases such as thioglycolic acid, thioacetic acid, and other mercamtans. Permanent waving processes typically use substances based on thioglycolate, whereas permanent hair straighteners (also known as "relaxers") normally require more aggressive reducing chemicals, e.g., hydroxides, in order to achieve "permanent", straightening.

Among reagents used for the purpose of fixation of hair, i.e., compounds capable of re-establishing the physicomechanical properties of the hair by forming disulfide and other cross links between keratin chains, hydrogen peroxide ($H_2O_2$) is the most commonly used reagent as $H_2O_2$ reacts rapidly with the keratin —SH groups. Other examples of commonly used oxidizing agents are perborates, bromates, chlorites, iodates, bromates, persulphates and tetrathionates. These oxidative agents often over-oxidize and damage the hair, producing sulphonic acids such as cysteic acid instead of simply reforming disulfide bridges.

Hydrogen peroxide is also the conventional catalyst in is hair dyeing formulas, and it is important to recognize that peroxide concentrations used for hair dyeing formulas are significantly larger than those used to reform hair cross links in the oxidative, restorative phase of a hair setting treatment (also used at different pH).

It is possible, and not uncommon in home straightening treatments, to use atmospheric oxygen as an oxidizing agent for reformation of hair cross links. The direct use of atmospheric oxygen, however, suffers from the disadvantage that several hours are required in order to complete the reaction. This option is even less appealing when used in conjunction with permanent waving treatments, since hair fixation should occur while the hair is in the desired conformation; i.e., while the hair is on curlers.

Many consumers would like to apply a permanent dye at the same time as a permanent hair straightening (or waving) treatment. Unfortunately, this combination causes severe damage to the hair, primarily because the damage caused by exposure to high levels of $H_2O_2$ (i.e., more than 1% $H_2O_2$, such as those used in conventional hair dyes) is exacerbated when hair is in a damaged and vulnerable state as a result of exposure to strong reducing agents. For this reason, consumers are advised to wait at least two weeks between permanent straightening and permanent dyeing of hair. While temporary hair dyes can be applied to hair directly after a straightening treatment, there is a long-standing need and desire for a product that allows simultaneous permanent straightening and permanent dyeing of hair without excessive hair damage.

Permanent hair dyes are durable to sunlight, shampooing, and other hair treatments and are ordinarily refreshed periodically (about once a month) as new hair grows out. With these dyeing systems, the dyes are created directly in and on the hair. Small aromatic colourless dye precursors (e.g., p-phenylenediamine and o-aminophenol) penetrate deep into the hair where the precursors are oxidized by an oxidizing agent into colored polymeric compounds. These colored compounds are larger than the dye precursors and are not easily washed out of the hair.

Traditionally, $H_2O_2$ is used in concentrations of about 1–10%, normally from about 3–6%, as the oxidizing agent. The use of $H_2O_2$ in dye compositions has some disadvantages as $H_2O_2$ damages the hair. Further, conditions frequently used for oxidative dyeing require treatment at high pH (normally around pH 9–10), which also causes damage to the hair.

To overcome the disadvantages of using $H_2O_2$, it has been suggested to use oxidation enzymes to replace $H_2O_2$.

U.S. Pat. No. 3,251,742 (Revlon) describes a method for dyeing human hair by dye formation in situ (i.e., on the hair). An oxidative enzyme is used for the colour formation reactions at a substantially neutral pH (pH 7–8.5). Laccases, tyrosinases, polyphenolases and catacolases are mentioned as suitable oxidation enzymes.

EP patent No. 504.005 (Perma S. A.) concerns compositions for hair dyeing which do not require the presence of $H_2O_2$ (hydrogen peroxide). The compositions comprise an enzyme capable of catalysing the formation of the polymeric dyes and also dye precursors, such as bases and couplers, in a buffer solution wherein the pH of the composition is between 6.5 and 8 and the enzyme has an optimal activity in the same pH range.

A method for enzyme-mediated dyeing of keratinous fibres, such as hair, has been described in WO 97/19999 (Novo Nordisk) and WO 97/19998 (Novo Nordisk).

Canadian patent 67:93913 discloses a composition containing a metal-containing dye for simultaneously permanent waving and dyeing hair. EP patent No. 328816 describes a process for dyeing of waved or relaxed hair using a metal ion-catalyzed hair dyeing composition.

There is still a need for a commercially viable method that allows (i.e., can be performed without significantly damaging the hair) simultaneous permanent setting (straightening or waving) and permanent dyeing of hair, with sufficient depth and permanence of color on hair.

A method that permits simultaneous permanent dyeing and setting of hair will give consumers a new range of options in their hair style choices. In particular, it will increase convenience for consumers, who will no longer have to wait weeks after a permanent setting treating prior to dyeing their hair.

SUMMARY OF THE INVENTION

The object of the present invention is to provide an improved method for permanent dyeing of chemically reduced hair such that the dyeing is suitably permanent, and sufficiently mild such that it does not cause significant damage to hair and can be performed immediately following, or, preferably, during a hair setting treatment. The present invention thus fulfills a long-standing industry need for a method that can provide permanent dyeing on chemically reduced hair without significant damage, thereby allowing a combined permanent setting and dyeing treatment.

It is advantageous to dye the reduced hair as an integrated component of a hair setting treatment not only to provide convenience for the customer, but also because the enzyme-mediated oxi- is dative process is an active and beneficial component in reformation of hair cross links, and dyeing of reduced hair is enhanced (both depth and permanence of color) relative to dyeing of hair in its normal, oxidized state.

The inclusion of small amounts of hydrogen peroxide or functional equivalents enhances dyeing of reduced hair relative to enzyme-mediated dyeing treatments not incorporating $H_2O_2$.

The present invention can be applied as part of a permanent hair waving or straightening process, preferably as part of a straightening process.

The present invention provides a method for treating reduced hair comprising contacting said hair with a composition comprising at least one oxidoreductase, at least one mediator, and at least one chemical oxidizing agent in an amount equivalent to 0.001–1% hydrogen peroxide calculated by weight of the composition.

It is also an object of the invention to provide a method for treating hair comprising
1) chemically reducing covalent disulfide linkages in the hair, and
2) contacting said hair with a composition comprising at least one oxidoreductase, at least one mediator, and at least one chemical oxidizing agent in an amount equivalent to 0.001–1% hydrogen peroxide calculated by weight of the composition.

Furthermore, it is an object of the invention to provide a method for treating hair comprising
1) chemically reducing covalent disulfide linkages in the hair,
2) mechanically straightening said hair, and
3) contacting said hair with a composition comprising at least one oxidoreductase, at least one mediator, and at least one chemical oxidizing agent in an amount equivalent to 0.001–1% hydrogen peroxide calculated by weight of the composition.

Example of chemical oxidizing agents are hydrogen peroxide, bromate, and other oxidants that generate hydrogen peroxide in situ such as percarbonates and perborates.

Cysteic acid quantification is frequently used to assess hair damage in oxidized hair. The cysteic acid assay described in the "Materials and Methods" section below is used to determine the extent of damage to hair. The hair is considered to be significantly damaged when the assayed value is higher than 1.00 mole-%. When the value is less than 1.00 mole-%, preferably less than 0.75 mole-%, the hair is not considered to be significantly damaged. Therefore, in the context of the present invention, a "mild composition" is a composition that does not damage the hair significantly as defined above.

The term "reduced" hair covers hair that has been subjected to a chemical reducing agent such that the amount of sulfhydryl groups in hair (primarily cysteine in its reduced, non-oxidized state) is at least three times higher than the normal level in comparable hair that has not been subjected to a reducing process. The amount of sulfhydryl groups in the hair can be s estimated using the thiol content assay described in the "Materials and Methods" section.

The term "straightened" hair covers hair that has been subjected to a chemical reduction treatment and has been mechanically oriented in a straight fashion, e.g., by combing. This definition covers both hair that has been subjected to a complete permanent hair straightening treatment, i.e., reduced and mechanically straightened hair that has been undergone oxidative fixation to reform cross links, and is therefore no longer in a reduced state, as well as hair that has only undergone a is partial or incomplete straightening treatment, i.e., hair that has been chemically reduced and mechanically straightened, but not subjected to an oxidative fixation (or may be in the middle of the slow process of air oxidation), and thus remains in a reduced state.

In general, the dyeing step is integrated into the hair straightening process by being applied within one day, preferably within one hour, even more preferably directly following removal (by rinsing) of the reducing agent.

In a preferred embodiment, the concentration of said chemical oxidant such as hydrogen peroxide is sufficient to enhance depth and permanence of color on hair, relative to systems containing only oxidoreductases, as well as to aid in reformation of hair cross links typically reduced in the first stage of a hair straightening process, but insufficient for permanent hair dyeing in the absence of oxidoreductase, and insufficient to cause significant damage to hair. According to the invention the chemical oxidizing agent is used in an amount equivalent to 0.001–1%, preferably 0.01–0.5%, calculated by weight of the dyeing formulation.

DETAILED DESCRIPTION OF THE INVENTION

Figure 1:
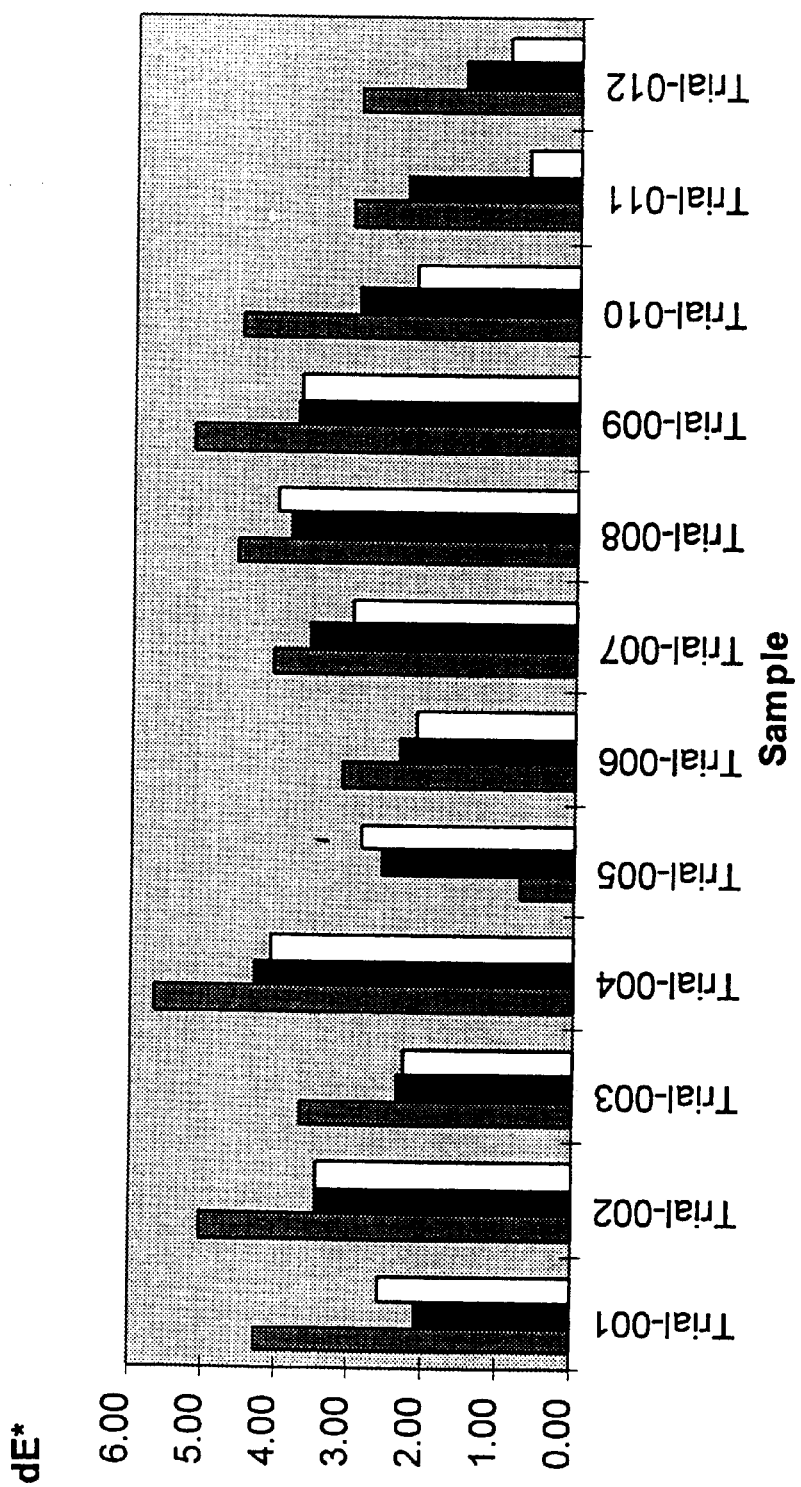
FIG. 1 shows the results of various hair dyeing experiments using dye compositions of the present invention.

As used in this specification and the appended claims, the singular forms "a", "an", and "the", include plural references unless the context clearly dictates otherwise. Thus, for example, reference to an "oxidoreductase" include mixtures of oxidoreductases. Unless defined otherwise, all technical and scientific terms used herein have the same meaning as commonly understood by one of ordinary skill in the art to which the invention applies.

The term "ingredients used in setting compositions" means is ingredients known by the skilled person with skill in the field of formulating hair care composition to be incorporated in prior art compositions.

Oxidoreductases

Oxidoreductases (i.e., enzymes classified under the Enzyme Classification number E.C. 1 (Oxidoreductases) in accordance with the Recommendations (1992) of the International Union of Bio-chemistry and Molecular Biology (IUBN)) are enzymes that catalyze redox reactions.

According to the invention, three types of oxidoreductases are especially contemplated:

a) Laccases or related enzymes cover enzymes which act on molecular oxygen ($O_2$) and yield water ($H_2O$) without any need for peroxide (e.g. $H_2O_2$), b) Oxidases cover enzymes which act on molecular oxygen ($O_2$) and yield peroxide (e.g. $H_2O_2$), and c) Peroxidases cover enzymes which act on peroxide (e.g. $H_2O_2$) and yield water ($H_2O$).

Preferred oxidoreductases are of microbial origin, especially recombinant and/or substantially purified enzymes without any substantial side activity. Microbialenzymes are preferred to plant and fruit enzymes as they can be produced more easily in large amounts by recombinant techniques known in the art.

The term "microbial enzyme" in the context of the present invention refers to enzymes derived from bacteria, filamentous fungi or yeasts.

In the case of an enzyme acting on oxygen ($O_2$) as the acceptor, said oxygen may be molecular oxygen supplied by the air. In a preferred embodiment, part of the oxygen is provided by a foam produced from a hair setting/hair dyeing composition comprising a foaming agent.

Suitable enzymatic foam compositions for hair dyeing which may be used according to the invention include hair-dyeing compositions that comprise foaming agent selected from soaps and anionic, cationic, non-ionic, amphoteric, sugar surfactants and/or zwitterionic surfactants and mixtures thereof. The foaming agent(s) may be present at levels of from 0.1% to 15%, preferably from 0.2 to 13%, more preferably from 0.25 to 10%, e.g., from 0.5 to 8% by weight of the final composition. Examples of anionic surfactants suitable for use as the foaming agent are soaps, e.g., in the form of alkali or ethanolamine, isopropanol 2-methyl-2-amino-1,3-propanediol salts of fatty acids such as laurate, myristate, palmitate, stearate, isostearate, behenate, oleate, linoleate, etc.; fatty alcohol ether sulfates such as sodium lauryl ether sulfate; fatty alcohol sulfates such as sodium lauryl sulfate (SLS and SDS); sulfo succinates, e.g. dioctyl sodium sulfo succinate; α-olefin sulfonates; alkyl amide ether sulfates; fatty acid condensation products; alkyl ether phosphates and monoglyceride sulfates. Examples of nonionic surfactants suitable for use as the foaming agent are especially the nonionic fatty acids and fatty amines that often are s used as foam stabilizers, thickeners and boosters, e.g. fatty acid alkanol amides and dialkanol amides and fatty acid alkanol amide polyglycol ethers and fatty amine oxides. Examples of amphoteric surfactants suitable for use in combination with anionic surfactants as the foaming agent are alkyl betaines, alkyl imidazolinium betaines, alkyl sulfo betaines, amidoalkyl betaines, N-alkyl-β-amino propionates, etc.

Examples of foaming agents in the form of sugar surfactants include (a) alkyl- and/or alkenyloligoglycosides and/or (b) fatty acid-N-alkylpolyhydroxyalkylamides. The alkyl- and/or alkenyloligoglycoside (a) has the formula:

R1—O—[G]p    (I), in which R1=4–22C alkyl and/or alkenyl group, G=a sugar residue with 5 or 6C and p=1–10. The fatty acid-N-alkylpolyhydroxyalkylamide (b) has the formula:

R2CO—N(R3)—[Z]    (II), in which R2CO=a 6–22C aliphatic acyl residue, R3=H, alkyl or hydroxyalkyl with 1–4C and [Z]=a linear or branched polyhydroxyalkyl residue with 3–12C and 3–10 OH groups;

a) alkyl and alkenyl oligoglycosides of formula R1—O[G]p (I) and b) alkali and/or alkali metal salts of 12–22C secondary 2,3-alkyl sulphates (II). R1=4–22C alkyl and/or alkenyl; G=5–6C sugar residue; p=1–10. The wt. ratio (I):(II) is pref. 1:99–99:1; and (A) fatty acid-N-alkyl polyhydroxyalkyl amides; and
(B) sugar surfactants of: (B1) saccharose esters, (B2) sorbitan esters and/or (B3) polysorbates.

A sugar surfactant may also comprise 10–40% (wt.) alkyl and/or alkenyl-oligoglucoside of the formula

R1—O—[G]p    (II),

10–40% alkyl- and/or alkenyl-oligoglucoside of the formula

R2—O—(G)p    (III), and 80–20% alkyl ether sulphate of the formula

R3-(OCH2CH2)nO—SO3M    (IV)

in which R1=8–11C alk(en)yl; (G)=a glucose gp.; p=1–10; (1–3) R2=12–22C alk(en)yl; R3=6–22C alk(en)yl; M=an alkali(ne earth), ammonium or alkanolammonium ion; (pref. Na, Mg) n=1–20 2–7. Pref. R2, R3=12–14C alkyl; and polyglycerine fatty acid ester polyoxyalkylene ether RR1R2R3N+—CH(Y)—CH2-O—CH2-C(CH3)2-C(OH)(H)—C(=O)—NH—CH2-CH2-OHX— (I) where R, R1, R2=1–24C alkyl or 8–24C alkenyl; R3=1–18C alkylene; X=monovalent (in)organic anion; and Y=OH or H; and 1–5 wt.% of fatty alcohol polyglycol ether, 1–5% of Guerbet alcohol, 1–5% of polyol partial ester, (B) 1–5% of anionic polymer, (C) 15–30% of fatty alcohol polyglycol ether sulphate, (D) 15–30% of alkyloligoglycoside; and sulphated prods. of fatty acid-N-alkylpolyhydroxyalkyl amides of formula R1CO—N(R2)—Z (I), R1CO= 6–22C aliphatic acyl; R2=H, 1–4C alkyl or 1–4C hydroxyalkyl; Z=3–12C polyhydroxyalkyl contg. 3–10 hydroxy gps; and sugar surfactant solubilisers selected from alkyl oligoglycosides of formula (I) and carboxylic acid N-polyhydroxyalkylamides of formula (II). RI—O(G)p (I) R2CO—NR3-Z (II) R1=opt. hydroxylated 1–8C alkyl; G=5C or 6C sugar residue; p=1–10; R2CO= 1–8C aliphatic acyl; R3=H, 1–8C alkyl or 1–8C hydroxyalkyl; Z=3–12C polyhydroxyalkyl contg. 3–10 OH gps.

Examples of preferred foaming agents are SDS (sodium dodecyl sulfate), sodium dodecyl ether sulfate and soaps.

It may also be desired to add other additives that function as stabilizers, boosters and thickeners, for example one or more compounds selected from fatty acid alkanol amides, dialkanol amides or fatty alkanol amides, polyglycol ethers such as ethoxylated lauric acid monoethanol amide, or fatty amine oxides such as alkyl dimethyl amine oxide. In connection with an anionic surfactants such as SDS, it will often be preferred to use an amphoteric surfactant such as betaine phosphate.

Also, enzyme systems which comprise a combination of more than one enzyme among the three types of enzymes are contemplated according to the invention. The enzyme systems may e.g. consist of a laccase or a related enzyme and an oxidase; a laccase or a related enzyme and a peroxidase; a laccase or a related enzyme, an oxidase and a peroxidase;or an oxidase and a peroxidase.

Laccases and Related Enzymes

Laccases (benzenediol:oxygen oxidoreductases) (E.C. class 1.10.3.2 according to Enzyme Nomenclature (1992)

Academic Press, Inc) are multi-copper containing enzymes that catalyse the oxidation of phenols. Laccase-mediated oxidations result in the production of aryloxy-radical intermediates from suitable phenolic substrates; the ultimate coupling of the intermediates so produced provides a combination of dimeric, oligomeric, and polymeric reaction products. Certain reaction products can be used to form dyes suitable for dyeing keratinous fibres (see below).

Moreover, the intermediate aryloxy-radical intermediates may themselves possess oxidative properties which may be utilised in e.g. re-formation of disulfide linkages in keratinous fibres of e.g. hair (see below).

Examples of specifically contemplated enzymes within the group of laccases and related enzymes which are capable of oxidizing keratin —SH groups and hence re-forming keratin disulfide cross linkages are mono- and diphenolic oxidases, such as catechol oxidase (1.10.3.1), laccase (E.C. 1.10.3.2), tyrosinase (E.C. 1.14.18.1), and bilirubin oxidase (E.C. 1.3.3.5).

Suitable laccases may, for example, be derived from a strain of Polyporus sp., in particular a strain of *Polyporus pinsitus* (also called *Trametes villosa*) or *Polyporus versicolor*, or a strain of Myceliophthora sp., e.g. *M. thermophila* or a strain of Rhizoctonia sp., in particular a strain of *Rhizoctonia praticola* or *Rhizoctonia solani*, or a strain of Scytalidiumn sp., in particular *S. thermophilium*, or a strain of Pyricularia sp., in particular *Pyricularia oryzae*, or a strain of Coprinus sp., such as is a *C. cinereus*.

The laccase may also be derived from a fungus such as Collybia, Fomes, Lentinus, Pleurotus, Aspergillus, Neurospora, Podospora, Phlebia, e.g. *P. radiata* (WO 92/01046), Coriolus sp., e.g. *C. hirsitus* (JP 2-238885), or Botrytis.

In a preferred embodiment of the invention the laccase is derived from a strain of Myceliophthora sp., especially the *Myceliophthora thermophila laccase* described in WO 95/33836 (Novo Nordisk).

When using a laccase, such as the *M. thermophila laccase*, for re-forming keratinous fibre cross links, possibly with simultaneous keratinous fibre dyeing, the invention may be carried out at room temperature, preferably around the optimum temperature of the enzyme, at a pH in the range from 3.0 to 9.0, preferably in the range from 4.0 to 8.0, especially in the range from 6.0 to 8.0.

Bilirubin oxidase may be derived from a strain of Myrothecium sp., such as a strain of *M. verrucaria*.

Peroxidases

Peroxidases are used in combination with either $H_2O_2$ or an oxidase to obtain the desired result, i.e., re-formation of keratin disulfide cross-linkages in e.g. hair.

Suitable peroxidases can be found within the group of enzymes acting on peroxide as acceptor, e.g. E.C. 1.11.1, especially peroxidase (E.C. 1.11.1.7).

Specific examples of suitable enzymes acting on peroxide as acceptor include peroxidases derived from a strain of the fungus Coprinus, in particular a strain of *Coprinus cinereus* or *Coprinus macrorhizus*, or derived from a strain of the bacteria Bacillus, is in particular a strain of *Bacillus pumilus*.

Haloperoxidases are also suitable according to the invention. Haloperoxidases form a class of enzymes which are able to oxidise halides ($Cl^-$, $Br^-$, $I^-$) in the presence of hydrogen peroxide to the corresponding hypohalous acids. A suitable haloperoxidase is derivable from Curvularia sp., in particular *C. verruculosa*.

Oxidases

Oxidases yielding peroxide ($H_2O_2$) are used in combination with a peroxidase to remove or at least reduce the peroxide produced. Suitable oxidases include glucose oxidase (E.C. 1.1.3.4), hexose oxidase (E.C. 1.1.3.5), L-amino-acid oxidase (E.C. 1.4.3.2), xylitol oxidase, galactose oxidase (E.C. 1.1.3.9), pyranose oxidase (E.C. 1.1.3.10) and alcohol oxidase (E.C. 1.1.3.13).

If an L-amino acid oxidase is used, it may be derived from a Trichoderma sp. such as *Trichoderma harzianum*, such as the L-amino acid oxidase described in WO 94/25574 (from Novo Nordisk A/S), or *Trichoderma viride*.

A suitable glucose oxidase may originate from Aspergillus sp., such as a strain of *Aspergillus niger*, or from a strain of Cladosporium sp. in particular *Cladosporium oxysporum*.

Hexose oxidases from the red sea-weed *Chondrus crispus* (commonly known as Irish moss) (Sullivan and Ikawa, (1973), Biochim. Biophys. Acts, 309, p. 11–22; Ikawa, (1982), Meth. in Enzymol. 89, carbohydrate metabolism part D, 145–149) oxidise a broad spectrum of carbohydrates, such as D-glucose, D-galactose, maltose, cellobiose, lactose, D-glucose 6-phosphate, D-mannose, 2-deoxy-D-glucose, 2-deoxy-D-galactose, D-fructose, D-glucuronic acid, and D-xylose.

Also the red sea-weed *Iridophycus flaccidum* produces easily is extractable hexose oxidases which oxidise several different mono- and disaccharides (Bean and Hassid, (1956), J. Biol. Chem, 218, p. 425; Rand et al. (1972), J. of Food Science 37, p. 698–710).

Another suitable enzyme group is xylitol oxidase (see e.g. JP 80892242) which oxidises xylitol, D-sorbitol, D-galactitol, D-mannitol and D-arabinitol in the presence of oxygen. A xylitol oxidase can be obtained from strains of Streptomyces sp. (e.g. Streptomyces IKD472, FERM P-14339). Said enzyme has a pH optimum at 7.5 and is stable at pH 5.5 to 10.5 and at temperatures up to 65° C.

Mediators

In the present context, the term "mediator" is intended to mean an agent capable of acting as a substrate of oxidoreductases, and includes compounds commonly referred to in the art as "precursors" and "modifiers", as well as "enhancing agents" Therefore, this term includes (i) compounds generally used with oxidoreductases to provide a strong color base; (ii) compounds capable of modifying colors produced with other mediators, although incapable of providing substantial color on their own; (iii) compounds that normally have a bleaching effect.

Examples of mediators capable of enhancing the activity of oxidoreductases include the compounds described in WO 95/01426, which is hereby incorporated by reference, and represented by the general formula I:

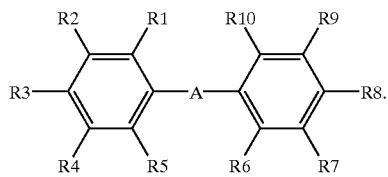

Specifically contemplated compounds within the above formula I include the following: 2,2'-azino-bis(3-ethylbenzothiazoline-6-sulfonate (ITS); 6-hydroxy-2-naphtoic acid; 7-methoxy-2-naphtol; 7-amino-2- naphthalene sulfonic acid; 5-amino-2-naphthalene sulfonic acid; 1,5-diaminonaphthalene; 7-hydroxy-1,2-naphthimidazole; 10-methylphenothiazine; 10-phenothiazine-propionic acid (PPT); N-hydroxysuccinimide-10-phenothiazine-propionate; benzidine; 3,3'-dimethylbenzidine; 3,3'-dimethoxybenzidine; 3,3',5,5'-tetramethylbenzidine; 4'-hydroxy-4-biphenylcarboxylic acid; 4-amino-4'-methoxystilbene; 4,4'-diaminostilbene-2,2'-disulfonic acid; 4,4'-diaminodiphenylamine; 2,7-diaminofluorene; 4,4'-dihydroxybiphenylene; triphenylamine; 10-ethyl-4-phenothiazinecarboxylic acid; 10-ethylphenothiazine; 10-propylphenothiazine; 10-isopropylphenothiazine; methyl-10-phenothiazinepropionate; 10-phenylphenothiazine; 10-allylphenothiazine; 10-phenoxazinepropionic acid (POP); 10-(3-(4-methyl-1-piperazinyl)propyl)phenothiazine; 10-(2-pyrrolidinoethyl) phenothiazine; 10-methylphenoxazine; iminostilbene; 2-(p-aminophenyl)-6-methylbenzothiazole-7-sulfonic acid; N-benzylidene-4-biphenylamine; 5-amino-2-naphthalenesulfonic acid; 7-methoxy-2-naphtol; 4,4'-dihydroxybenzophenone; N-(4-(dimethylamino) benzylidene)-p-anisidine; 3-methyl-2-benzothiazolinone(4-(dimethylamino)benzylidene)hydrazone; 2-acethyl-10-methylphenothiazine; 10-(2-hydroxyethyl)phenothiazine; 10-(2-hydroxyethyl)phenoxazine; 10-(3-hydroxypropyl) phenothiazine; 4,4'-dimethoxy-N-methyl-diphenylamine, and vanillin azine.

Other mediators contemplated include 4-hydroxybenzoic acid, L-tyrosine, syringate acids, ferulic acid, sinapic acid, chlorogenic acid, caffeic acid and esters thereof.

Still further examples include organic compounds described in WO 96/10079, which is hereby incorporated by reference, and represented by the general formula II:

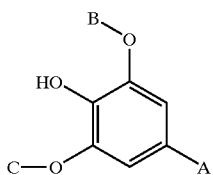

(Specific compounds covered by the above formula II are acetosyringone, syringaldehyde, methylsyringate, syringic acid, ethylsyringate, propylsyringate, butylsyringate, hexylsyringate, octylsyringate and ethyl 3-(4-hydroxy-3,5-dimethoxyphenyl)acrylate.

Precursors are defined herein as mediators that are converted into colored compounds by oxidation. Precursors may be compounds belonging to one of three major chemical families: the diamines, aminophenols (or aminonaphtols), heterocyclic bases and the phenols.

Furthermore, a number of indole or indoline derivative precursors are disclosed in WO 94/00100, and other suitable benzoic acid precursors are disclosed in WO 98/15257 (Novo Nordisk). Said precursors mentioned in these documents are hereby incorporated herein by reference.

Examples of such suitable precursors include compounds from the group comprising o-phenylene-diamine, p-phenylene-diamine (pPD), p-toluylene-diamine, chloro-p-phenylenediamine, p-aminophenol, o-aminophenol, 3-methyl-4-aminophenol and 3,4-diaminotoluene, 2-methyl-1,4-diaminobenzene, 4-methyl-o-phenylenediamine, 2-methoxy-p-phenylenediamine, 2-chloro-1,4-diamino-benzene, 4-amino diphenylamine, 1-amino-4-β-methoxyethylamino-benzene, 1-amino-4-bis-(β-hydroxyethyl)-aminobenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-benzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, such as 4,7-phenazinedicarboxylic acid, 2,7-phenazinedicarboxylic acid, 2-phenazinecarboxylic acid, 2,7-diaminophenazine, 2,8-diaminophenazine, 2,7-diamino-3,8-dimethoxyphenazine, 2,7-diamino-3-methoxyphenazine, 2,7-diamino 3-methoxyphenazine, 3-dimethyl 2,8-phenazinediamine, 2,2'-[(8-amino-7-methyl-2-phenazinyl)imino]bis-ethanol, 2,2'-[(8-amino-7-methoxy-2-phenazinyl)imino]bis-ethanol, 2,2'-[(8-amino-7-chloro-2-phenazinyl)imino]bis-ethanol, 2-[(8-amino-7-methyl-2-phenazinyl)amino]-ethanol, 2,2'-[(8-amino-2-phenazinyl)imino]bis-ethanol, 3-amino-7-(dimethylamino)-2,8-dimethyl-5-phenyl-chloride, 9-(diethylamino)-benzo[a]phenazine-1,5-diol, N-[8-(diethylamino)-2-phenazinyl]-methanesulfonamide, N-(8-methoxy-2-phenazinyl)-methanesulfonamide, N,N,N',N'-tetramethyl-2,7-phenazinediamine, 3,7-dimethyl-2-phenazinamine, p-amino benzoic acids, such as p-amino benzoic acid ethyl, p-amino benzoic acid glycerid, p-amino benzoic acid isobutyl, p-dimethylamino benzoic acid amil, p-dimethylamino benzoic acid octyl, p-diethoxy amino benzoic amil, p-dipropoxy amino benzoic acid ethyl, acetylsalicylic acid, and isatin derivatives, such as 2,3-diamino benzoic acid, and mixtures of the above precursors.

Specifically contemplated mixtures of mediators include the mixtures published in DK patent appln. no. 358/98 (see especially the table in FIGS. 1 to 3).

Also incorporated by reference are precursors disclosed in WO 99/36034, 99/36035, 99/36036, 99/36037, 99/36038, 99/36039, 99/36040, 99/36041, 99/36042, 99/36043, 99/36044, 99/36045 and 99/36046.

Among the paraphenylenediamines discloses herein that can be used as precursors in colouring compositions corresponding to the invention, especially the following formula compounds (I) and their acid addition salts can be mentioned:

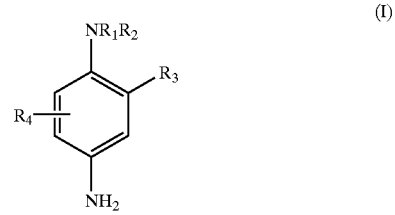

in which:
R$_1$ represents a hydrogen atom, a C$_1$–C$_4$ alkyl radical, monohydroxyalkyl C$_1$–C$_4$, polyhydroxyalkyl C$_2$–C$_4$, alcoxy(C$_1$–C$_4$)alkyl(C$_1$–C$_4$), C$_1$–C$_4$ alkyl substituted by a nitrogen, phenyl or 4'-aminophenyl group;
R$_2$ represents a hydrogen atom, a C$_1$–C$_4$ alkyl radical, monohydroxyalkyl C$_1$–C$_4$, polyhydroxyalkyl C$_2$–C$_4$, alcoxy(C$_1$–C$_4$)alkyl(C$_1$–C$_4$) or C$_1$–C$_4$ alkyl substituted by a nitrogen group;
R$_3$ represents a hydrogen atom, a halogen atom such as a chlor, brom, iod or fluor atom, a C$_1$–C$_4$ alkyl radical, monohydroxyalkyl C$_1$–C$_4$, hydroxyalcoxy C$_1$–C$_4$, acetylaminoalcoxy $C_1$–$C_4$, mesylaminoalcoxy $C_1$–$C_4$ or carbamoylaminoalcoxy $C_1$–$C_4$, $R_4$ represents a hydrogen atom, halogen atom or a $C_1$–$C_4$ alkyl radical.

Among the nitrogen groups of the above formula (I) especially the amino, monoalkyl($C_1$–$C_4$)amino, dialkyl ($C_1$–$C_4$)amino, trialkyl($C_1$–$C_4$)amino, monohydroxyalkyl ($C_1$–$C_4$)amino, imidazolinium and ammonium radicals can be mentioned.

Among the paraphenylenediamines of the above formula (I) one can more specifically mention paraphenylenediamine, paratoluylenediamine, 2-chloro paraphenylenediamine, 2,3-dimethyl paraphenylenediamine, 2,6-dimethyl paraphenylenediamine, 2,6-diethyl paraphenylenediamine, 2,6-dimethyl paraphenylenediamine, N,N-dimethyl paraphenylenediamine, N,N-diethyl paraphenylenediamine, N,N-dipropyl paraphenylenediamine, 4-amino N,N-diethyl 3-methyl aniline, N,N-bis-(β-hydroxyethyl) paraphenylenediamine, 4-N,N-bis-(β-hydroxyethyl)amino 2-methyl aniline, 4-N,N-bis-(β-hydroxyethyl)amino 2 chloro aniline, 2-β-hydroxyethyl paraphenylenediamine, 2-fluoro paraphenylenediamine, 2-isopropyl paraphenylenediamine, N-(β-hydroxypropyl) paraphenylenediamine, 2-hydroxymethyl paraphenylenediamine, N,N-dimethyl 3-methyl paraphenylenediamine, N,N-(ethyl, β-hydroxyethyl) paraphenylenediamine, N-(β,γ-dihydroxypropyl) paraphenylenediamine, N-(4'-aminophenyl) paraphenylenediamine, N-phenyl paraphenylenediamine, 2-β-hydroxyethyloxy paraphenylenediamine, 2-β-acetylaminoethyloxy paraphenylenediamine, N-(β-methoxyethyl)paraphenylenediamine and their acid addition salts.

Among the paraphenylenediamines of the above formular (I), preferred are: paraphenylenediamine, paratoluylenediamine, 2-isopropyl paraphenylenediamine, 2-β-hydroxyethyl paraphenylenediamine, 2-β-hydroxyethyloxy paraphenylenediamine, 2,6-dimethyl paraphenylenediamine, 2,6-diethyl paraphenylenediamine, 2,3 dimethyl paraphenylenediamine, N,N-bis-(β-hydroxyethyl)paraphenylenediamine, 2-chloro paraphenylenediamine, 2-β-acetylaminoethyloxy paraphenylenediamine, and their acid addition salts.

Also incorporated are precursors with the following formula (II) and their acid addition salts:

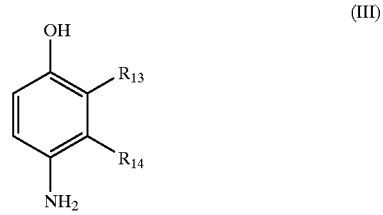

In which:
a) $Z_1$ and $Z_2$, identical or different, represent a hydroxyl radical or $3NH_2$ which can be substituted with a $C_1$–$C_4$ alkyl radical or by Y;
b) Y represents an alkylene chain comprising 1 to 14 carbon atoms, linear or branched interrupted or terminated by one or more nitrogen groups and/or by one or more hetero atoms such as oxygen, sulphur or nitrogen possible substituted by one or more hydroxyl radicals or $C_1$–$C_6$ alkoxy;

c) $R_5$ et $R_6$ represent a hydrogen atom or halogen atom, a $C_1$–$C_4$ alkyl radical, monohydroxyalkyl $C_1$–$C_4$, polyhydroxyalkyl $C_2$–$C_4$, aminoalkyl $C_1$–$C_4$ or Y;
d) $R_7$, $R_8$, $R_9$, $R_{10}$, $R_{11}$ and $R_{12}$, identical or different, represent a hydrogen atom, Y or $C_1$–$C_4$ alkyl radical;

Among the nitrogen groups of formular (II) the amino radicals, monoalkyl($C_1$–$C_4$)amino, dialkyl($C_1$–$C_4$)amino, trialkyl($C_1$–$C_4$)amino, monohydroxyalkyl($C_1$–$C_4$)amino, imidazoliniumet ammonium are especially mentioned.

Among the precursors of formular (II) N,N'-bis(β-hydroxyethyl) N,N'-bis(4'-aminophenyl) 1,3-diamino propanol, N,N'-bis-(β-hydroxyethyl) N,N'-bis-(4'-aminophenyl)ethylenediamine, N,N'-bis-(4-aminophenyl) tetramethylenediamine, N,N'-bis-(β-hydroxyethyl) N,N'-bis-(4-aminophenyl)tetramethylenediamine, N,N'-bis-(4,4-methylaminophenyl)tetramethylenediamine, N,N'-bis-(ethyl) N,N'-bis-(4'-amino, 3'-methylphenyl) ethylenediamine, 1,8-bis-(2,5-diaminophenoxy)-3,5-dioxaoctane, and their acid addition salts are more especially mentioned.

Among the precursors of formular (II), N,N'-bis-(βhydroxyethyl) N,N'-bis-(4'-aminophenyl) 1,3-diamino propanol, 1,8-bis-(2,5-diaminophenoxy)-3,5-dioxaoctane or one of their acid addition salts are particularly preferred.

Among the para-aminophenols discloses herein that can be used as precursors in colouring compositions corresponding to the invention, especially, the following formula compounds (III) and their acid addition salts can be mentioned:

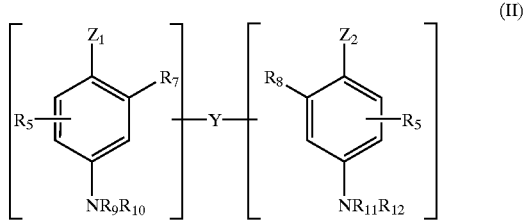

in which:
e) $R_{13}$ represents a hydrogen or halogen atom, a $C_1$–$C_4$ alkyl radical, monohydroxyalkyl $C_1$–$C_4$, alcoxy ($C_1$–$C_4$)alkyl($C_1$–$C_4$), aminoalkyl $C_1$–$C_4$ or hydroxyalkyl($C_1$–$C_4$)aminoalkyl $C_1$–$C_4$,
f) $R_{14}$ represents a hydrogen or halogen atom, a $C_1$–$C_4$ alkyl radical, monohydroxyalkyl $C_1$–$C_4$, polyhydroxyalkyl $C_1$–$C_4$, aminoalkyl $C_1$–$C_4$, cyanoalkyl $C_1$–$C_4$ or alcoxy($C_1$–$C_4$)alkyl($C_1$–$C_4$),
at least one of radicals $R_{13}$ or $R_{14}$ represent a hydrogen atom.

Among the para-aminophenols of formular (III) especially the para-aminophenol, 4-amino 3-methyl phenol, 4-amino 3-fluoro phenol, 4-amino 3-hydroxymethyl phenol, 4-amino 2-methyl phenol, 4-amino 2-hydroxymethyl phenol, 4-amino 2-methoxymethyl phenol, 4-amino 2-aminomethyl phenol, 4-amino 2-(β-hydroxyethyl aminomethyl)phenol, 4-amino 2-fluoro phenol, and their acid addition salts.

Among the orthoaminophenols that can be used as precursors especially 2-amino phenol, 2-amino 5-methyl phenol, 2-amino 6-methyl phenol, 5-acetamido 2-amino phenol, and their acid addition salts can be mentioned.

Among the heterocyclic bases used as precursors especially pyridine derivatives, pyrimidine derivatives, pyrazole derivatives, pyrazolo-pyrimidine derivatives, and their acid addition salts can be mentioned.

Among the pyridine derivatives, especially those disclosed in e.g. GB 1 026 978 and GB 1 153 196 can be mentioned, such as 2,5-diamino pyridine, 2-(4-methoxyphenyl)amino 3-amino pyridine, 2,3-diamino 6-methoxy pyridine, 2-(β-methoxyethyl)amino 3-amino 6-methoxy pyridine, 3,4-diamino pyridine, and their acid addition salts can be mentioned.

Among the pyrimidine derivatives, especially those disclosed in e.g. DE 2 359 399 or JP 88-169 571 and JP 91-333 495 or in WO 96/15765 can be mentioned, such as 2,4,5, 6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine and their acid addition salts.

Also disclosed are 4,5-diamino 6-hydroxy pyrimidine.

Among the pyrazole derivatives, especially those disclosed in DE 3 843 892, DE 4 133 957 and WO 94/08969, WO 94/08970, FR-A-2 733 749 and DE 195 43 988 can be mentioned, such as 4,5-diamino 1-methyl pyrazole, 3,4-diamino pyrazole, 4,5 diamino 1-(4'-chlorobenzyl)pyrazole, 4,5-diamino 1,3-dimethyl pyrazole, 4,5-diamino 3-methyl 1-phenyl pyrazole, 4,5 diamino 1-methyl 3-phenyl pyrazole, 4-amino 1,3-dimethyl 5-hydrazino pyrazole, 1-benzyl 4,5-diamino 3-methyl pyrazole, 4,5-diamino 3-tert-butyl 1-methyl pyrazole, 4,5-diamino 1-tert-butyl 3-methyl pyrazole, 4,5-diamino 1-(β-hydroxyethyl) 3-methyl pyrazole, 4,5-diamino 1-ethyl 3-methyl pyrazole, 4,5 diamino 1-ethyl 3-(4'-methoxyphenyl)pyrazole, 4,5-diamino 1-ethyl 3-hydroxymethyl pyrazole, 4,5-diamino 3-hydroxymethyl 1-methyl pyrazole, 4,5-diamino 3-hydroxymethyl 1-isopropyl pyrazole, 4,5-diamino 3-methyl 1-isopropyl pyrazole, 4-amino 5-(2'-aminoethyl) amino 1,3-dimethyl pyrazole, 3,4,5-triamino pyrazole, 1-methyl 3,4,5-triamino pyrazole, 3,5-diamino 2-methyl 4-methylamino pyrazole, 3,5-diamino 4-(β-hydroxyethyl) amino 1-methyl pyrazole, and their acid addition salts.

Also disclosed are 3,4-diamino hydroxy pyrazole.

Among the pyrazolo-pyrimidine derivatives, especially the pyrazolo-[1,5-a]-pyrimidines with the following formula (IV), their acid/base addition salts and their tautomers, when they exsists in a tautomeric equilibrium:

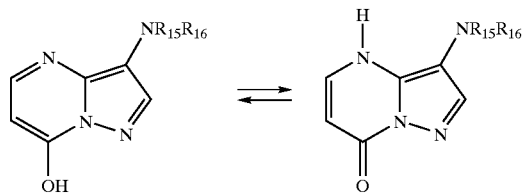

(IV)

in which:

R$_{15}$, R$_{16}$, R$_{17}$, et R$_{18}$, identical or different, represent a hydrogen atom, an C$_1$–C$_4$ alkyl radical, an aryl radical, a hydroxyalkyl radical C$_1$–C$_4$, a polyhydroxyalkyl radical C$_1$–C$_4$, a radical (C$_1$–C$_4$)alcoxy alkyl C$_1$–C$_4$, an aminoalkyl radical C$_1$–C$_4$ (the amine can be protected by a acetyl radical, ureido or sulfonyle), a (C$_1$–C$_4$) alkylamino alkyl radical C$_1$–C$_4$, a di-[(C$_1$–C$_4$)alkyl]-amino alkyl radical C$_1$–C$_4$ (the dialkyls may form a cyclic carbon or a heterocyclic with 5 or 6 link), a hydroxy(C$_1$–C$_4$)alkyl-radical or di-[hydroxy(C$_1$–C$_4$) alkyl]-amino alkyl radical C$_1$–C$_4$;

The radicals X, identical or different, represent a hydrogen atom, a C$_1$–C$_4$ alkyl radical, an aryl radical, a hydroxyalkyl en C$_1$–C$_4$, a polyhydroxyalkyl radical C$_2$–C$_4$, an amino alkyle radical C$_1$–C$_4$, a (C$_1$–C$_4$)alkyl amino alkyl radical C$_1$–C$_4$, a di-[(C$_1$–C$_4$)alkyl]amino alkyle radical C$_1$–C$_4$ (the dialkyls may form a cyclic carbon or a heterocyclic with 5 or 6 link), a hydroxy (C$_1$–C$_4$)alkyl radical or di-[hydroxy(C$_1$–C$_4$)alkyl] amino alkyl radical C$_1$–C$_4$, an amino radical, a (C$_1$–C$_4$) alkyl- or di-[(C$_1$–C$_4$)alkyl]-amino radical; a halogen atom, a carboxyl acid group, a sulfonic group;

i is 0, 1, 2 or 3;

p is 0 or 1 q is 0 or 1 n is 0 or 1 with the provision that:

the sum p+q does not equal 0;

when p+q is 2, n=0 and the groups NR$_{15}$R$_{16}$ and NR$_{17}$R$_{18}$ occupy positions (2,3); (5,6); (6,7); (3,5) or (3,7);

when p+q is 1, n=1 and the group NR$_{15}$R$_{16}$ (or NR$_{17}$R$_{18}$) and the group OH occupy positions (2,3); (5,6); (6,7); (3,5) or (3,7);

When the pyrazolo-[1,5-a]pyrimidines of formula (IV) comprises a hydroxyl group in one of the positions 2,5 or 7 en α d'un atome d'azote, their exist an tautomeric ecuilibrium represented by the following scheme:

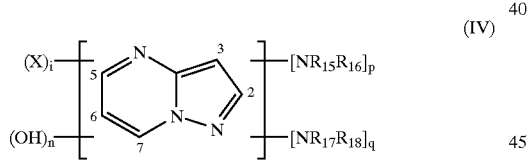

Among the pyrazolo-[1,5-a]-pyrimidines of formula (IV) the following can especially be mentioned:

pyrazolo-[1,5-a]-pyrimidine-3,7-diamine;

2,5-dimethyl pyrazolo-[1,5-a]-pyrimidine-3,7-diamine;

pyrazolo-[1,5-a]-pyrimidine-3,5-diamine;

2,7-dimethyl pyrazolo-[1,5-a]-pyrimidine-3,5-diamine;

3-amino pyrazolo-[1,5-a]-pyrimidin-7-ol 3-amino pyrazolo-[1,5-a]pyrimidin-5-ol 2-(3-amino pyrazolo-[1,5-a]-pyrimidin-7-ylamino)-ethanol 2-(7-amino pyrazolo-[1,5-a]-pyrimidin-3-ylamino)-ethanol 2-[(3-Amino-pyrazolo[1,5-a]pyrimidin-7-yl)-(2-hydroxy-ethyl)-amino]-ethanol 2-[(7-Amino-pyrazolo[1,5-a]pyrimidin-3-yl)-(2-hydroxy-ethyl)-amino]-ethanol 5,6-dimethyl pyrazolo-[1,5-a]-pyrimidine-3,7-diamine;

2,6-dimethyl pyrazolo-[1,5-a]-pyrimidine-3,7-diamine;

2,5, N7, N7-tetramethyl pyrazolo-[1,5-a]-pyrimidine-3,7-diamine;

and their acid addition slats and their tautomers, when they exist in a tautomeric equilibrium.

Pyrazolo-[1,5-a]-pyrimidines of the formula (IV) can be prepared as disclosed in the following references

EP 628559 BEIERSDORF-LILLY

R. Vishdu, H. Navedul, Indian J. Chem., 34b (6), 514, 1995.

N. S. Ibrahim, K. U. Sadek, F. A. Abdel-Al, Arch. Pharm., 320, 240, 1987.

R. H. Springer, M. B. Scholten, D. E. O'Brien, T. Novinson, J. P. Miller, R. K. Robins, J. Med. Chem., 25, 235, 1982.

T. Novinson, R. K. Robins, T. R. Matthews, J. Med. Chem., 20, 296, 1977.

U.S. Pat. No. 3,907,799 ICN PHARMACEUTICALS

The pyrazolo-[1,5-a]-pyrimidines of formula (IV) can also be prepared as disclosed in the following references:

A. McKillop et R. J. Kobilecki, Heterocycles, 6(9), 1355, 1977.

E. Alcade, J. De Mendoza, J. M. Marcia-Marquina, C. Almera, J. Elguero, J. Heterocyclic Chem., 11(3), 423, 1974.

K. Saito, I. Hori, M. Higarashi, H. Midorikawa, Bull. Chem Soc. Japan, 47(2), 476, 1974.

Also disclosed are pyrazolo-[1,5-a]-pyrimidine-3,7-diamine, 2-methyl pyrazolo-[1,5-a]-pyrimidine-3,7-diamine, 2,5-dimethyl pyrazolo-[1,5-a]-pyrimidine-3,7-diamine, pyrazolo-[1,5-a]-pyrimidine-3,5-diamine, 2,7-dimethyl pyrazolo-[1,5-a]pyrimidine-3,5-diatmine, 3-amino pyrazolo-[1,5-a]-pyrimidin-7-ol, 3-amino 5-methyl pyrazolo-[1,5-a]-pyrimidin-7-ol, 3-amino pyrazolo-[1,5-a]-pyrimidin-5-ol, 2-(3-amino pyrazolo-[1,5-a]-pyrimidin-7-ylamino)-ethanol, 3-amino-7-β-hydroxyethylamino-5-methyl-pyrazolo-[1,5-a]-pyrimidine, 2-(7-amino pyrazolo-[1,5-a]-pyrimidin-3-ylamino)-ethanol, 2-[(3-amino-pyrazolo-[1,5-a]-pyrimidin-7-yl)-(2-hydroxyethyl)-amino]-ethanol, 2-[/7-amino-pyrazolo-[1,5-a]-pyrimidin-3-yl)-(2-hydroxyethyl)-amino]-ethanol, 5,6-dimethyl pyrazolo-[1,5-a]-pyrimidine-3,7-diamine, 2,6-dimethyl pyrazolo-[1,5-a]-pyrimidine-3,7-diamine, 2,5, N-7, N-7-tetramethyl pyrazolo-[1,5-a]pyrimidine-3,7-diamine, and their acid addition salts and their tautomers.

The precursors is preferably present in amounts from 0,0005 to 12 wt-% based on he total weight of the dyeing composition, more preferably from 0,005 to 6 wt-%.

By including compounds referred to as modifiers (also known as couplers) in the dyeing composition, a number of color tints can be obtained. Cathecol and Resorcinol are examples of such modifiers. Modifiers are defined as a class of mediators that provides little color when oxidized in the absence of other mediators, but can significantly modify the generated colors when used in the presence of other mediators, in particular precursors.

Preferably, at least one modifier is used in combination with the oxidoreductase in the method of the invention, thereby allowing a number of color tints to be obtained. In general, modifiers are used in dyeing methods, as the colours resulting from hair dyeing without a modifier are usually unacceptable for most people.

Modifiers are typically m-diamines, m-aminophenols, or polyphenols, such as m-diphenols or a combination thereof. The modifiers may be heterocyclic or non-heterocyclic. The modifier reacts with mediators in the presence of the oxidative enzyme, converting it into a coloured compound.

Examples of heterocyclic modifiers include indoles, indolines, monocyclic pyrimidines and phenazines.

Examples of modifiers include m-phenylene-diamine, 2,4-diaminoanisole, 1-hydroxynaphthalene(α-naphthol), 1,4-dihydroxybenzene(hydroquinone), 1,5-dihydroxynapthalene, 1,2-di-hydroxybenzene (pyrocatechol), 1,3-dihydroxybenzene (resorcinol), 1,3-dihydroxy-2-methylbenzene, 1,3-dihydroxy-4-chlorobenzene(4-chlororesorcinol), 1,2,3, trihydroxybenzene, 1,2,4-trihydroxybenzene, 1,2,4-trihydroxy-5-methylbenzene and 1,2,4-trihydroxytoluene, and mixtures thereof.

Further examples of modifiers/couplers are 2-methyl-5-amino-phenol, 5-N-(β-hydroxyethyl)-amino-2-methyl-phenol, 3-amino-phenol, 1,3-dihydroxy-benzene, 1,3-dihydroxy-2-methyl-benzene,4-chloro-1,3-dihydroxy-benzene, 2,4-diamino-1-(β-hydroxyethyloxy)-benzene, 2-amino-4-(β-hydroxyethylamino)-1-methoxy-benzene, 1,3-diamino-benzene, 1,3-bis-(2,4-diaminophenoxy)-propane, sesamol, α-naphtol, 6-hydroxy-indole, 4-hydroxy-indole, 4-hydroxy-N-methyl-indole, 6-hydroxy-indoline, 2,6-dihydroxy-4-methyl-pyridine, 1-H-3-methyl-pyrazole-5-one, 1-phenyl-3-methyl-pyrazole-5-one, 2,6-dimethyl-pyrazolo-[1,5-b]-1,2,4-triazole, 2,6-dimethyl-[3,2-c]-1,2,4-triazole, 6-methyl-pyrazolo-[1,5-a]-benzimidazole, and their acid addition salts.

The couplers may be present in a amount of 0,0001 to 10 wt-% based on the total amount of the dyeing composition, preferably from 0,005 to 5 wt-%.

Among the meta-aminophenols discloses herein that can be used as couplers in colouring compositions corresponding to the invention, especially the following formula compounds (III) and their acid addition salts can be mentioned:

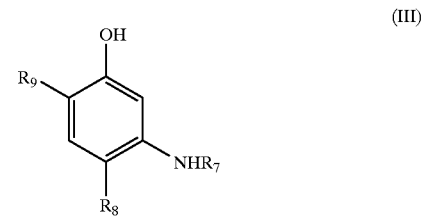

(III)

In which:

a) $R_7$ represents a hydrogen atom, an alkyl radical $C_1$–$C_4$, monohydroxyalkyl $C_1$–$C_4$ or polyhydroxyalkyl $C_2$–$C_4$, b) $R_8$ represents a hydrogen atom, an alkyl radical $C_1$–$C_4$, alcoxy $C_1$–$C_4$ or a halogen atom chosen from chlor, brom or fluor, c) $R_9$ represents a hydrogen atom, an alkyl radical $C_1$–$C_4$, alcoxy $C_1$–$C_4$, monohydroxyalkyl $C_1$–$C_4$, polyhydroxyalkyl $C_2$–$C_4$.

Among the meta-aminophenols of formula (III) especially meta-aminophenol, 5-amino 2-methoxy phenol, 5-amino 2-(β-hydroxyethyloxy)phenol, 5-amino 2-methyl phenol, 5-N-(β-hydroxyethyl)amino 2-methyl phenol, 5-N-(9-hydroxyethyl)amino 4-methoxy 2-methyl phenol, 5-amino 4-methoxy 2-methyl phenol, 5-amino 4-chloro 2-methyl phenol, 5-amino 2,4-imethoxy phenol, 5-(γ-hydroxypropylamino) 2-methyl phenol, and their acid addition salts can be mentioned.

Among the meta-aminophenols discloses herein that can be used as couplers in colouring compositions corresponding to the invention, especially the following formula compounds (IV) and their acid addition salts can be mentioned:

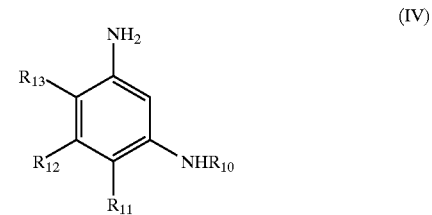

(IV)

In which:

d) $R_{10}$ represents a hydrogen atom, an alkyl radical $C_1$–$C_4$, monohydroxyalkyl $C_1$–$C_4$ or polyhydroxyalkyl $C_2$–$C_4$;

e) $R_{11}$ et $R_{12}$, identical or different, represent a hydrogen atom, an alkyl radical $C_1$–$C_4$, monohydroxyalcoxy $C_1$–$C_4$, or polyhydroxyalcoxy $C_2$–$C_4$;

f) $R_{13}$ represents a hydrogen atom, an alkoxy radical $C_1$–$C_4$, aminoalkoxy $C_1$–$C_4$, monohydroxyalkoxy $C_1$–$C_4$, polyhydroxyalkoxy $C_2$–$C_4$ or 2,4-diaminophenoxyalkoxy radical.

Among the meta-phenylenediamines of formula (IV) especially 2,4-diamino benzene, 3,5-diamino 1-ethyl 2-methoxybenzene, 3,5-diamino 2-methoxy 1-methyl benzene, 2,4-diamino 1-ethoxybenzene, 1,3-bis-(2,4-diaminophenoxy)propane, bis-(2,4-diaminophenoxy methane, 1-(β-aminoethyloxy) 2,4-diamino benzene, 2-amino 1-(β-hydroxyethyloxy) 4-methylamino benzene, 2,4-diamino 1-ethoxy 5-methyl benzene, 2,4-diamino 5-(β-hydroxyethyloxy) 1methylbenzene, 2,4-diamino 1-(β,γ-dihydroxypropyloxy)benzene, 2,4-diamino 1-(β-hydroxyethyloxy)benzene, 2-amino 4-N-(β-hydroxyethyl) amino 1-methoxy benzene, and their acid addition salts can be mentioned.

Among the meta-diphenols discloses herein that can be used as couplers in colouring compositions corresponding to the invention, especially the following formula compounds (V) and their acid addition salts can be mentioned:

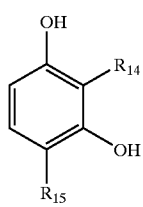

(V)

In which:
g) $R_{14}$ et $R_{15}$, identical or different, represent a hydrogen atom, an alkyl radical $C_1$–$C_4$ or a halogen atome chosen from chlor, brom or fluor.

Among the meta-diphenols of formula (V) especially 1,3-dihydroxy benzene, 2-methyl 1,3-dihydroxy benzene, 4-chloro 1,3-dihydroxy benzene, 2-chloro 1,3-dihydroxybenzene, and their acid addition salts can be mentioned.

Among the heterocyclic couplers according to the invention are derivatives of benzimidazole, benzomorpholine, sésamol, pyrazolo-azole, pyrrolo-azole, imidazoloazole, pyrazolo-pyrimidine, pyrazolin-3,5-diones, pyrrolo-[3,2-d]-oxazole, pyrazolo-[3,4-d]-thiazole, S-oxyde-thiazolo-azole, S,S-dioxyde-thiazolo-azole, and their acid addition salts.

Among the benzimidazole derivatives especially compounds of the following formula (I), and their acid addition salts can be mentioned:

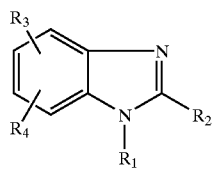

(I)

In which:
a) $R_1$ represents a hydrogen atom or an alkyl radical $C_1$–$C_4$,
b) $R_2$ represents a hydrogen atom, an alkyl radical $C_1$–$C_4$ or phenyle,
c) $R_3$ represents a hydroxyl radical, amino or methoxy,
d) $R_4$ represents a hydrogen atom, un hydroxyle radical, methoxy or alkyl $C_1$–$C_4$;

With the provision that:
e) when $R_3$ design an amino radical, it is in position 4,
f) when $R_3$ occupy position 4, then $R_4$ occupy position 7,
g) when $R_3$ occupy position 5, then $R_4$ occupy position 6.

Among the benzimidazole derivatives of formula (I) especially 4-hydroxy benzimidazole, 4-amino benzimidazole, 4-hydroxy 7-methyl benzimidazole, 4-hydroxy 2-methyl benzimidazole, 1-butyl 4-hydroxy benzimidazole, 4-amino 2-methyl benzimidazole, 5,6-dihydroxy benzimidazole, 5-hydroxy 6-methoxy benzimidazole, 4,7-dihydroxy benzimidazole, 4,7-dihydroxy 1-methyl benzimidazole, 4,7 dimethoxy benzimidazole, 5,6-dihydroxy 1-methyl benzimidazole, 5,6-dihydroxy 2-methyl benzimidazole, 5,6-dimethoxy benzimidazole, and their acid addition salts can be mentioned.

Among the benzomorpholine derivatives, especially compounds of the following formula (II), and their acid addition salts can be mentioned:

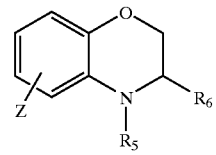

(II)

In which:
$R_5$ et $R_6$, identical or different, represent a hydrogen atom or an alkyl radical $C_1$–$C_4$,
Z represents a hydroxyl radical or amino.

Among the benzomorpholine derivatives of formula (ii) especially 6-hydroxy 1,4-benzomorpholine, N-methyl 6-hydroxy 1,4 benzomorpholine, 6-amino 1,4 benzomorpholine, and their acid addition salts can be mentioned.

Among the sésamol derivatives especially the following formula compounds (III) and their acid addition salts can be mentioned:

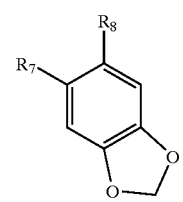

(III)

In which:
h) $R_7$ design a hydroxyl radical, amino, alkyl($C_1$–$C_4$) amino, monohydroxyalkyl($C_1$–$C_4$)amino or polyhydroxyalkyl($C_2$–$C_4$)amino,
i) $R_8$ design a hydrogen atom a halogen atome or an alcoxy radical $C_1$–$C_4$.

Among the sesamol derivatives of formula (III) especially 2-bromo 4,5-mehtylenedioxy phenol, 2-methoxy 4,5-methylenedioxy aniline, 2-(β-hydroxyethyl)amino 4,5 methylenedioxy benzene, and their acid addition salts can be mentioned.

Among the pyrazolo-azole derivatives especially the compounds disclosed in: FR 2 075 583, EP-A-119 860, EP-A-285 274, EP-A-244 160, EP-A-578 248, GB 1 58 377, U.S. Pat. No. 3,227,554, U.S. Pat. No. 3,419,391, U.S. Pat. No. 3,061,432, U.S. Pat. No. 4,500,630, U.S. Pat. No.

3,725,067, U.S. Pat. No. 3,926,631, U.S. Pat. No. 5,457,210, JP 84/99437, JP 83/42045, JP 84/162548, JP 84/171956, JP 85/33552, JP 85/43659, JP 85/172982, JP 85/190779 and the publications: Chem. Ber. 32 797 (1899), Chem Ber. 89, 2550, (1956), J. Chem. Soc. Perkin trans I, 2047, (1977), J. Prakt. Chem., 320, 533, (1978); can be mentioned which is hereby incorporated by reference.

More especially can be mentioned:

j) 2-methyl pyrazolo[1,5-b]-1,2,4-triazole, k) 2-ethyl pyrazolo[1,5-b]-1,2,4-triazole, l) 2-isopropyl pyrazolo[1,5-b]-1,2,4-triazole, m) 2-phenyl pyrazolo[1,5-b]-1,2,4-triazole, n) 2,6-dimethyl pyrazolo[1,5-b]-1,2,4-triazole, o) 7-chloro-2,6-dimethylpyrzolo[1,5-b]-1,2,4-triazole, p) 3,6-dimethyl-pyrazolo[3,2-c]-1,2,4-triazole, q) 6-phenyl-3-methylthio-pyrazolo[3,2-c]-1,2,4-triazole, r) 6-amino- pyrazolo[1,5-a]benzimidazole, and their acid addition salts.

Among the pyrrolo-azole derivatives especially the compounds disclosed in: U.S. Pat. No. 5,256,526, EP-A-557 851, EP-A-578 248, EP-A-518 238, EP-A-456 226, EP-A-488 909, EP-A-488 248, and the publications:

s) D. R. Liljegren Ber. 1964, 3436;

t) E. J. Browne, T.C.S., 1962, 5149;

u) P. Magnus, J.A.C.S., 1990, 112, 2465;

v) P. Magnus, J.A.C.S., 1987, 109, 2711;

w) Angew. Chem. 1960, 72, 956;

x) and Rec. Trav. Chim. 1961, 80, 1075; can be mentioned which is hereby incorporated by reference. More especially the following:

y)—5-cyano-4-ethoxycarbonyl-8-methyl pyrrolo[1,2-b]-1,2,4-triazole, z) 5-cyano-8-methyl-4-phenyl pyrrolo[1,2-b]-1,2,4-triazole, aa) 7-amino-6-ethoxycarbonyl pyrrolo[1,2-a]-benzimidazole, and their acid addition salts.

Among the imidazolo-azole derivatives especially those disclosed in: U.S. Pat. No. 5,441,863; JP 62-279 337; JP 06-236 011 et JP 07-092 632 can be mentioned which is hereby incorporated by reference.

More especially can be mentioned bb) 7,8-dicyano-imidazolo-3,2-a]-imidazole, cc) 7,8-dicyano-4-methyl-imidazolo-[3,2-a]-imidazole, and their acid addition salts.

Among the pyrazolo-pyrimidine derivatives especially those disclosed in EP-A-304 001 can be mentioned which is hereby incorporated by reference.

More especially the following can be mentioned:

dd) pyrazolo[1,5-a]pyrimidin-7-one, ee) 2,5-dimethyl pyrazolo[1,5-a]pyrimidin-7-one, ff) 2-methyl-6-ethoxycarbonyl pyrazolo[1,5-a]pyrimidin-7-one, gg) 2-methyl-5-methoxymethyl pyrazolo[1,5-a]pyrimidin-7-one, hh) 2-ter-butyl-5-trifluoromethyl pyrazolo[1,5-a]pyrimidin-7-one, ii) 2,7-dimethyl pyrazolo[1,5-a]pyrimidin-5-one, and their acid addition salts.

Among the pyrazolin-3,5-diones used as heterocyclic modifiers/couplers especially the compounds disclosed in: JP 07-036159, JP 07-084348 and U.S. Pat. No. 4,128,425 and in the publications:

jj) L. WYZGOWSKA, Acta. Pol. Pharm. 1982, 39 (1–3), 83 kk) E. HANNIG, Pharmazie, 1980, 35(4), 231 ll) M. H. ELNAGDI, Bull. Chem. Soc. Jap., 46(6), 1830, 1973 mm) G. Cardillo, Gazz, Chim. Ital. 1966, 96 (8–9), 973 can be mentioned which is hereby incorporated by reference.

Of pyrazolin-3,5-diones especially:

nn) 1,2-diphenyl pyrazolin-3,5-dione, oo) 1,2-diethyl pyrazolin-3,5-dione and their acid addition salts can be mentioned Among the pyrrolo-[3,2-d]-oxazole derivatived especially compounds disclosed in JP 07 325 375 can be mentioned which is hereby incorporated by reference.

Among the pyrazolo-[3,4-d]-thiazole derivatives especially the compounds disclosed in JP 07 244 361 and in J. Heterocycl. Chem. 16, 13 (1979) can be mentioned.

Among the S-oxyd-thiazolo-azole and S,S-dioxyd-thiazole-azole derivatives especially compounds disclosed in:

pp) JP 07 09 84 89, qq) Khim. Geterotsilk, Soedin, 1967, p. 93, rr) J. Prakt. Chem., 318, 1976, p. 12, ss) Indian J. Heterocycl. Chem. 1995, 5 (2), p. 135, tt) Acta. Pol. Pharm. 1995, 52 (5), 415, uu) Heterocycl. Commun. 1995, 1 (4), 297, vv) Arch. Pharm. (Weinheim, Ger.), 1994, 327 (12), 825 can be mentioned.

Also direct colors may be applied in combination with the precursors which direct colors are able to dye hair in the absence of precursors.

Direct cationic colors can be chosen from the cationic amino-anthraquinonic, the cationic mono- or di-azoic, the cationic naphtoquinones.

Examples are the chlorure [8-[(p-aminophenyl)azo]-7-hydroxy-2-naphtyl]trimethylammonium (Basic Brown 16 or Arianor Mahogany 306002 in the Color Index), the chlorure 3-[(4-amino-6-bromo-5,8-dihydro-1-hydroxy-8-imino-5-oxo-2-naphtalenyl)amino]-N,N,N-trimethyl-benzenaminium (Basic Blue 99 or Arianor Steel Blue 306004 in the Color Index), the chlorure 7-hydroxy-8-[(2-methoxyphenyl)azo]-N,N,N-trimethyl-2-naphtalenaminium (Basic Red 76 or Arianor Madder Red in the Color Index), the chlorure [8-[(4-amino-2-nitrophenyl)azo]-7-hydroxy-2-naphtyl]trimethylammonium (Basic Brown 17 or Arianor Sienna Brown 306001 in the Color Index) and the chlorure de 3-[(4,5-dihydro-3-methyl-5-oxo-1-phenyl-1H-pyrazol-4-yl)azo]-N,N,N-trimethyl-benzenaminium (Basic Yellow 57 or Arianor Straw Yellow 306005 in the Color Index).

The direct colors may be chosen from:

a) Compounds of formula (V):

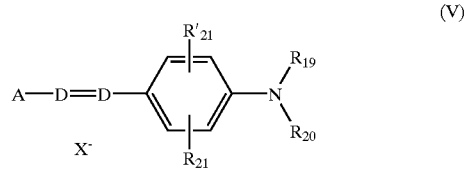

in which:

D represents a nitrogen atom or —CH, $R_{19}$ et $R_{20}$ identical or different, represent a hydrogen atom; an alkyl radical $C_1$–$C_4$ which can be substituted by —CN, —OH or —NH₂ or form with a carbon atom of a cyclic bezene a heterocyclic possibly oxygen or nitrogen, which can be substituted by one or more alkyl radicals $C_1$–$C_4$; a 4'-aminophenyl radical, $R_{21}$ et $R'_{21}$, identical or different, represent a hydrogen atom or halogen atom chosen from chlor, brom, iod, fluor, a cyano radical, alcoxy $C_1$–$C_4$ or acetyloxy, X represented an anion, preferably chosen from chlorure, methyl sulfate and acetate, A represents a group chosen from the following structures A1 to A19:

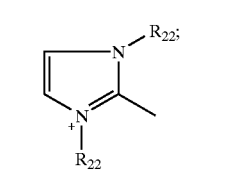
A₁

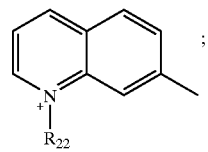
A₂

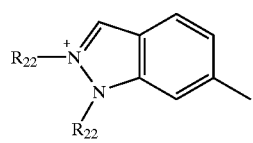
A₃

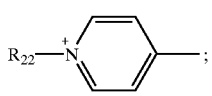
A₄

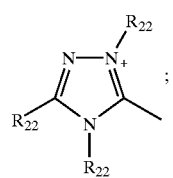
A₅

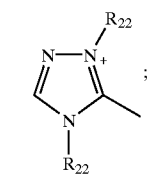
A₆

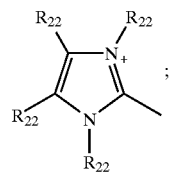
A₇

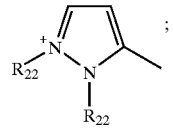
A₈

-continued

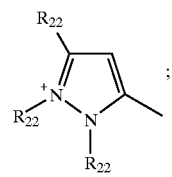
A₉

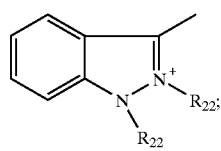
A₁₀

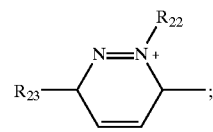
A₁₁

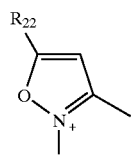
A₁₂

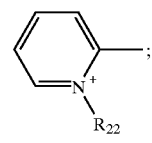
A₁₃

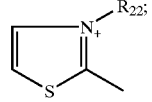
A₁₄

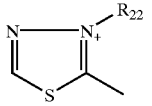
A₁₅

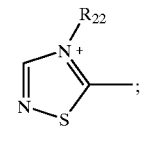
A₁₆

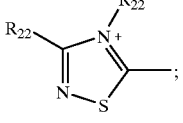
A₁₇

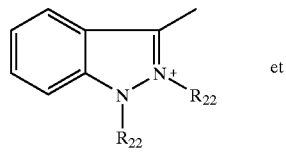 et
A₁₈

-continued

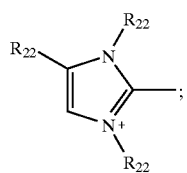
A19 in which $R_{22}$ represents a alkyl radical $C_1$–$C_4$ which can be subtituted by a hydroxyl radical and $R_{23}$ represents an alcoxy radical $C_1$–$C_4$;

b) compounds of formula (VI):

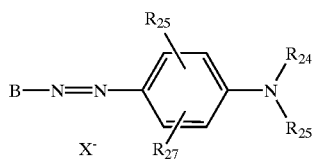
(VI)

in which:

$R_{24}$ represents a hydrogen atom or an alkyl radical $C_1$–$C_4$, $R_{25}$ represents a hydrogen atom, a alkyl radical which can be subtituted with —CN or amino, a 4-aminophenyl radical or together with $R_{24}$ form a heterocyclic compounds possibly oxygen and/or nitrogen which can be substituted with an alkyl radical $C_1$–$C_4$, $R_{26}$ et $R_{27}$, identical or different, represent a hydrogen atom, a halogen atom such as brom, chlor, iod or fluor, an alkyl radical $C_1$–$C_4$ or alcoxy $C_1$–$C_4$, —CN, X represent an anion, preferably chosen from chlorure, methyl sulfate and acetate, B represent a group chosen from the structures B1 to B6:

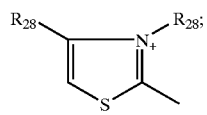
B1

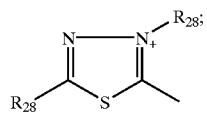
B2

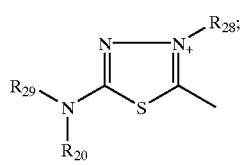
B3

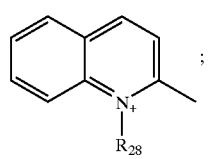
B4

-continued

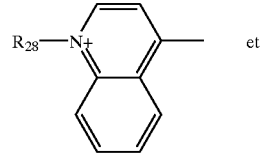
B5

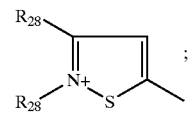
B6

In which $R_{28}$ represent a alkyl radical $C_1$–$C_4$; $R_{29}$ and $R_{30}$, identical or different, represent a hydrogen atom or an alkyl radical $C_1$–$C_4$;

c) Compounds of formula (VII) and (VII'):

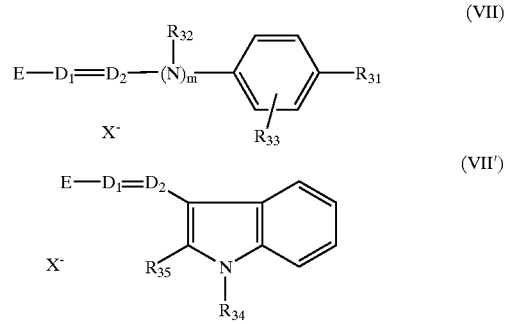

(VII)

(VII')

in which:

$R_{31}$ represent a hydrogen atom, an alcoxy radical $C_1$–$C_4$, a halogen atom such as brom, chlor, iod or fluor or a amino radical, $R_{32}$ represent hydrogen atom, an alkyl radical $C_1$–$C_4$, or forms with a cyclic benzene carbon atom un heterocyclic possibly oxygen and/or substituted with one or more alkyl groups $C_1$–$C_4$, $R_{33}$ represent a hydrogen atom or halogen such as brom, le chlor, iod or fluor, $R_{34}$ and $R_{35}$, identical or different, represent a hydrogen atom or an alkyl radical $C_1$–$C_4$, $D_1$ and $D_2$, identical or different, represent a nitrogen atom or —CH, m 0 or 1

X represent an anion preferably chosen from chlorur, methyl sulfate and acetate, E represent a group chosen from the structures E1 to E8:

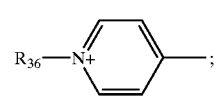
E1

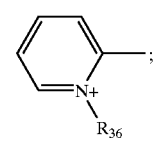
E2

-continued

E3 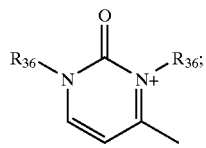

E4 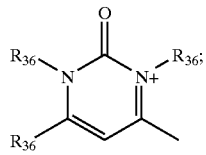

E5 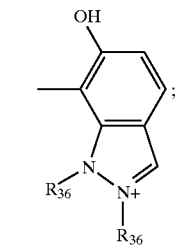

E6 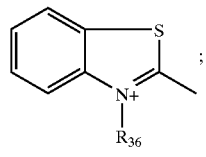

E7 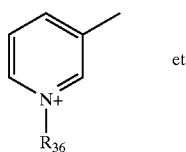

et 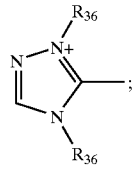

E8 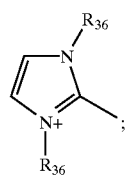

In which $R_{36}$ represent an alkyl radical $C_1$–$C_4$;
when m=0 and $D_1$ represent a nitrogen atom, then E may design a group with the structure E9:

E9 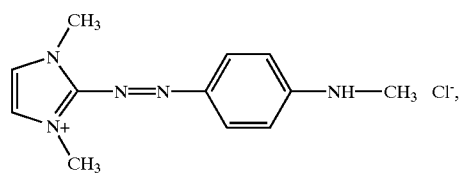

In which $R_{36}$ represent an alkyl radical $C_1$–$C_4$.

The direct cationic colors with the formula (V), (VI), (VII) and (VII') can be prepared as disclosed in WO 95/01772, WO 95/15144 et EP-A-0 714 954.

Among the direct cationic colors of formula (V) especially the following compounds with the structures (V1) to (V52) is mentioned:

(V1) 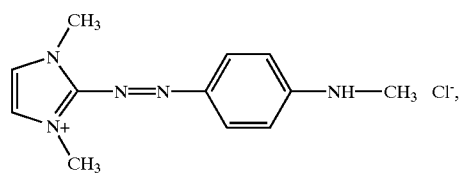

(V2) 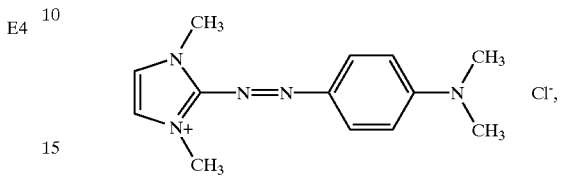

(V3) 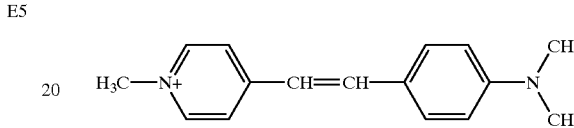

(V4) 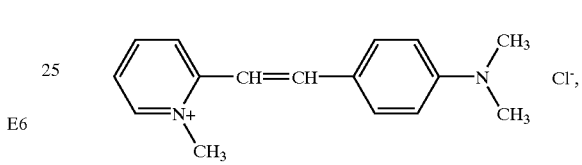

(V5) 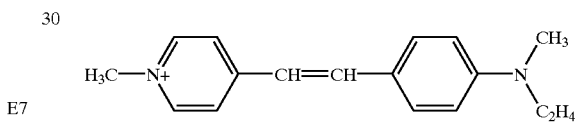

(V6) 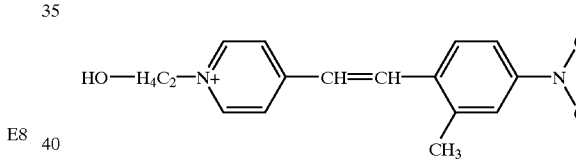

(V7) 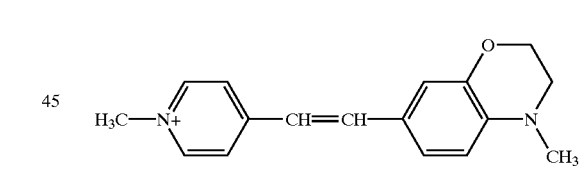

(V8) 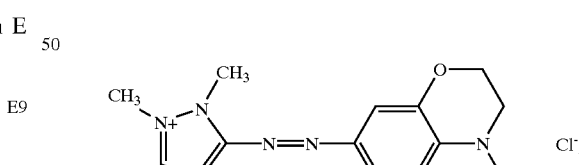

(V9) 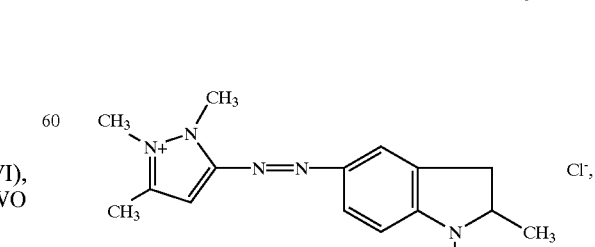

-continued
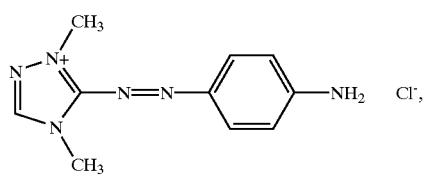 (V10)
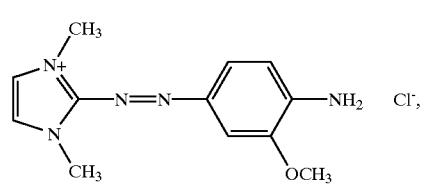 (V11)
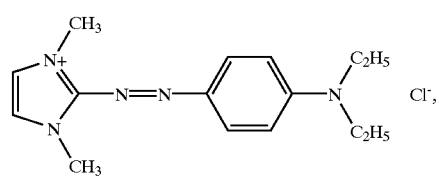 (V12)
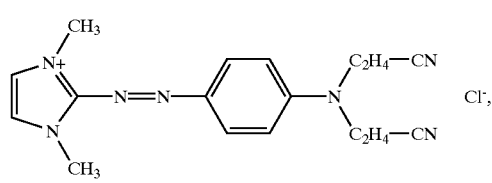 (V13)
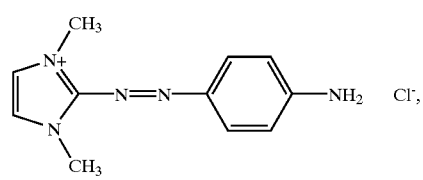 (V14)
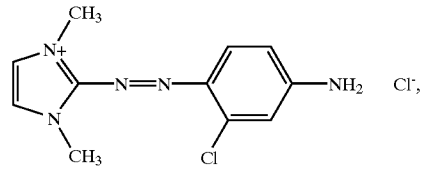 (V15)
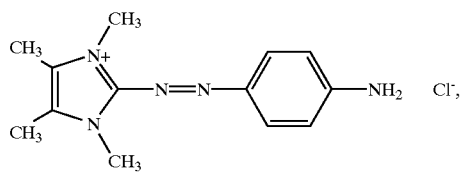 (V16)
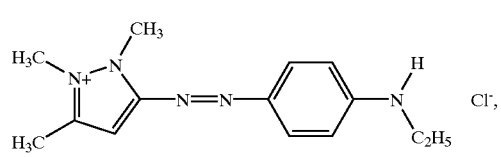 (V17)
-continued
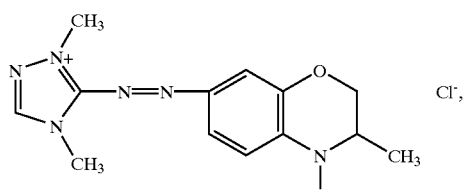 (V18)
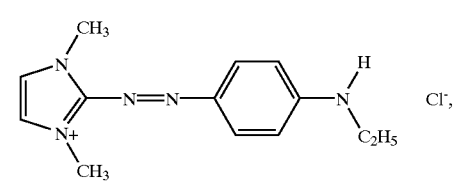 (V19)
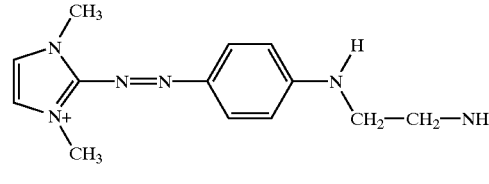 (V20)
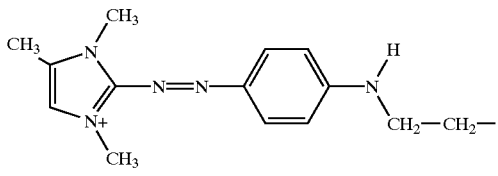 (V21)
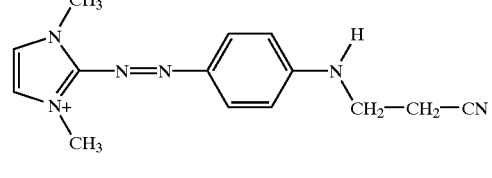 (V22)
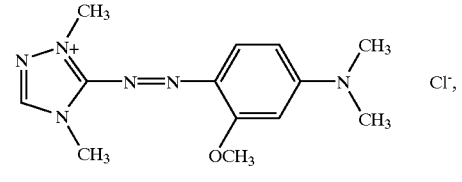 (V23)
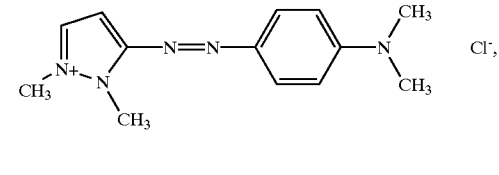 (V24)
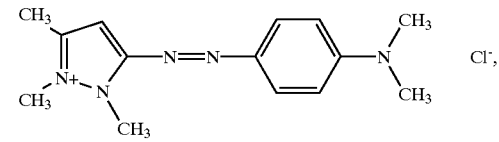 (V25)

-continued
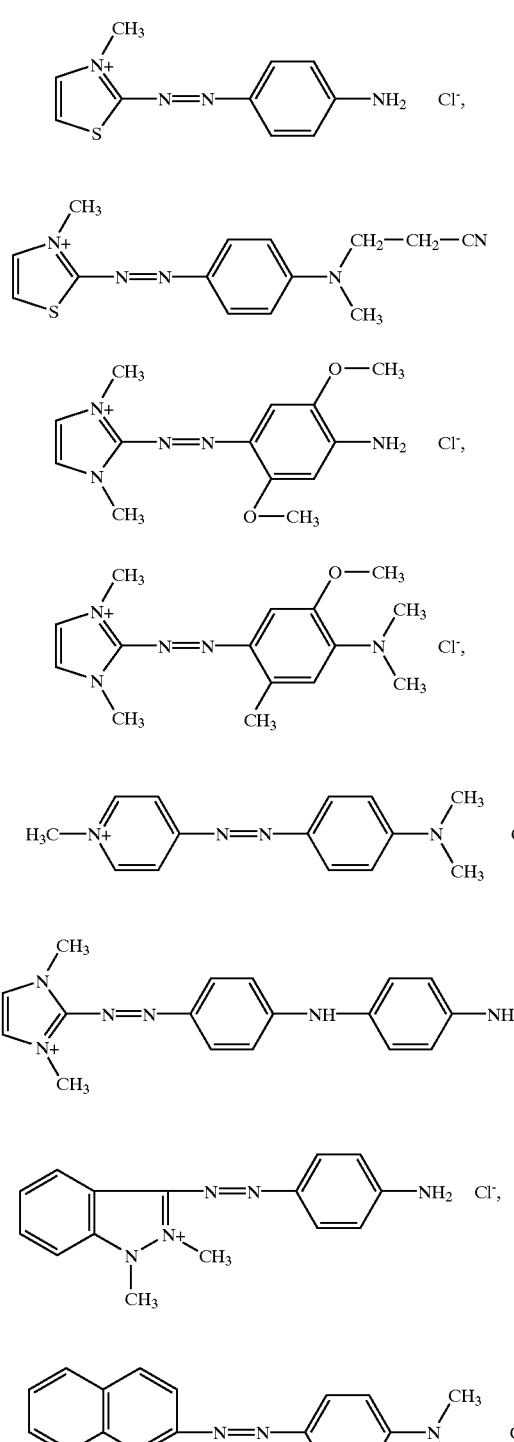
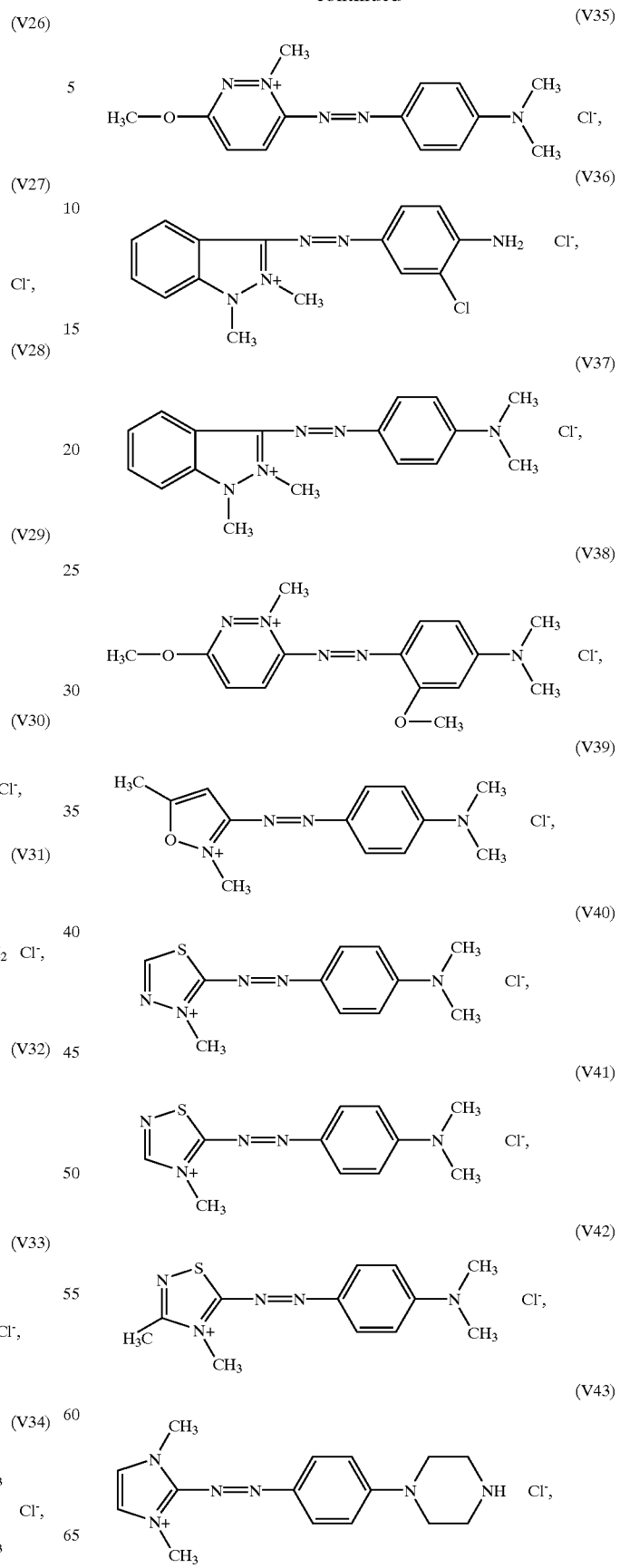

(V44)
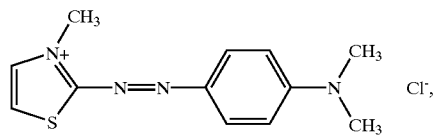
(V45)
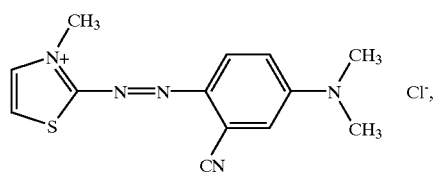
(V46)
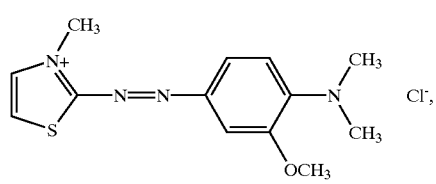
(V47)
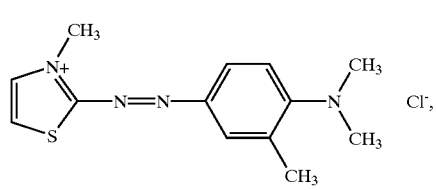
(V48)
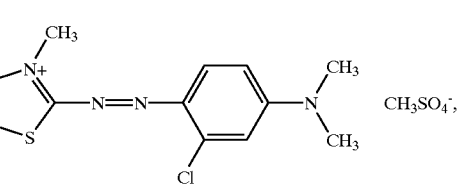
(V49)
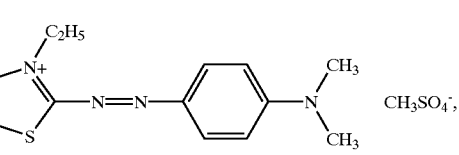
(V50)
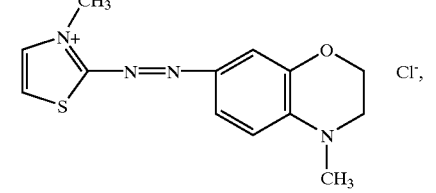
(V51)
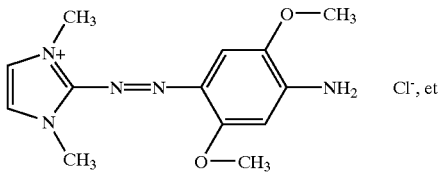
(V52)
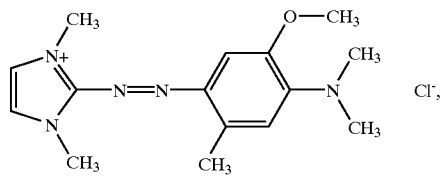
Among the compounds with the structures (V1) to (V52) especially preferred are structures (V1), (V2), (V4), (V14) and (V31).
Among the direct cationic colors with formula (VI) especially preferred are the following compounds with the structures (VI1) to (VI12):
(VI1)
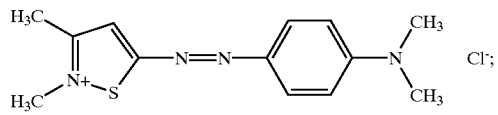
(VI2)
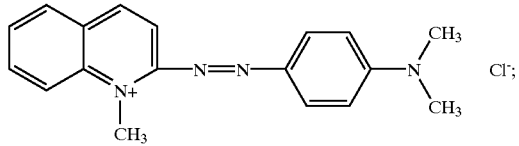
(VI3)
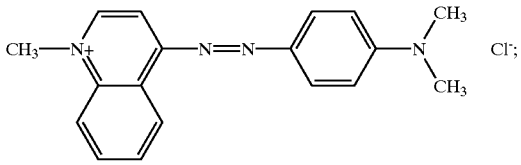
(VI4)
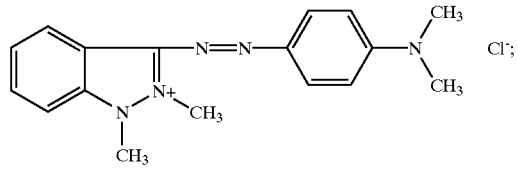
(VI5)
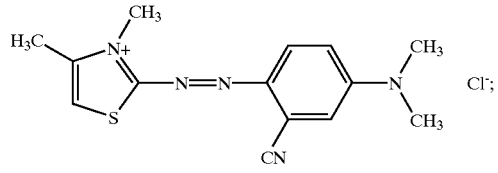
(VI6)
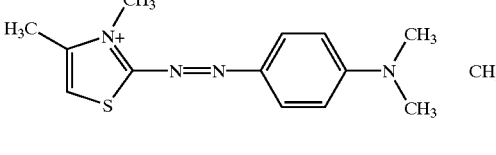
(VI7)
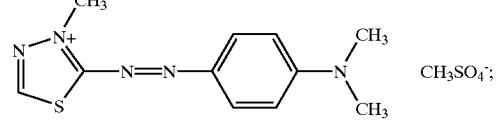

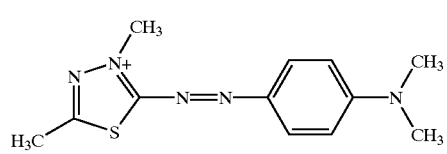 (VI8) CH₃SO₄⁻;
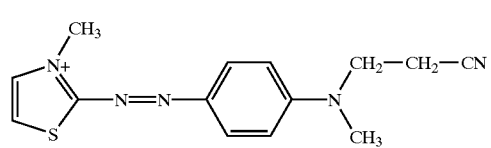 (VI9) Cl⁻;
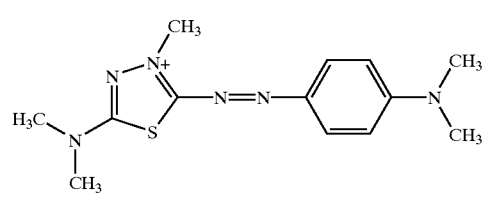 (VI10) CH₃SO₄⁻;
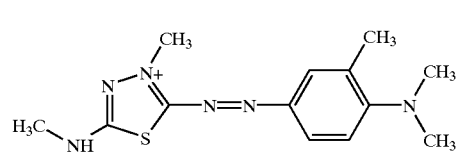 (VI11) CH₃SO₄⁻; et
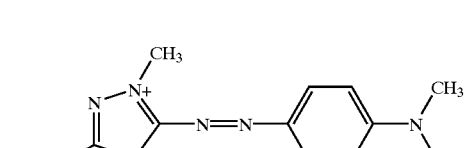 (VI12) CH₃SO₄⁻.
Among the direct cationic colors with formula (VII) especially preferred are the following compounds with structures (VII1) to (VII18):
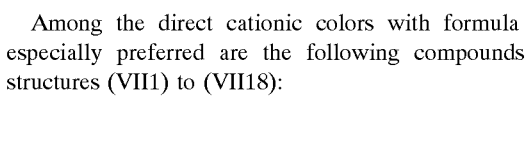 (VII1) Cl⁻;
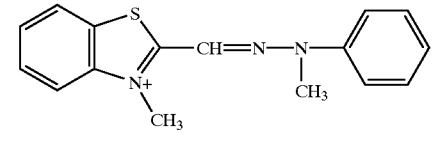 (VII2) Cl⁻;
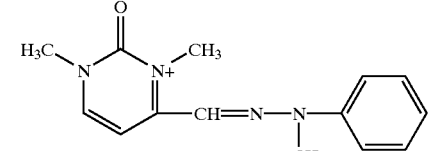 (VII3) Cl⁻;
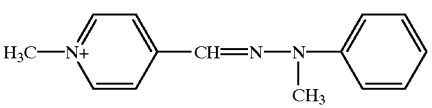 (VII4) CH₃SO₄⁻;
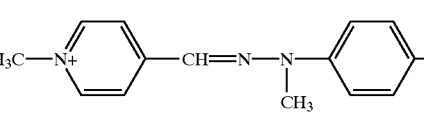 (VII5) Cl⁻;
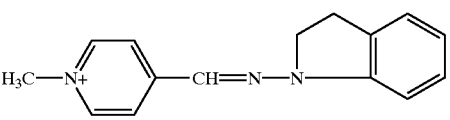 (VII6) CH₃SO₄⁻;
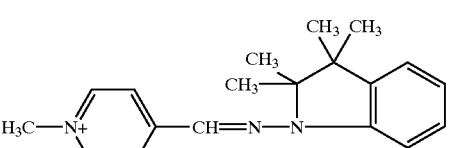 (VII7) CH₃SO₄⁻;
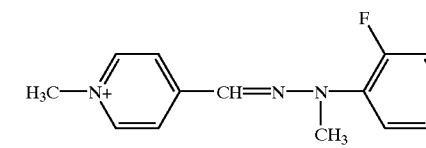 (VII8) Cl⁻;
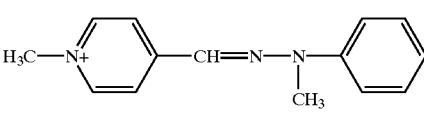 (VII9) Cl⁻;
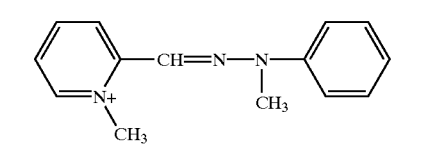 (VII10) CH₃SO₄⁻;
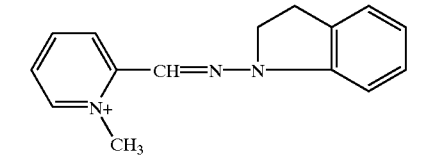 (VII11) CH₃SO₄⁻;
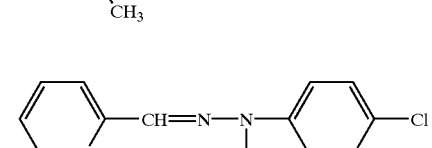 (VII12) CH₃SO₄⁻;
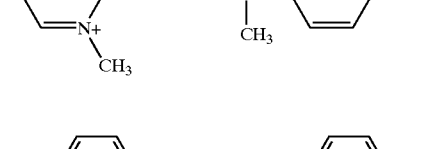 (VII13) CH₃SO₄⁻;

-continued

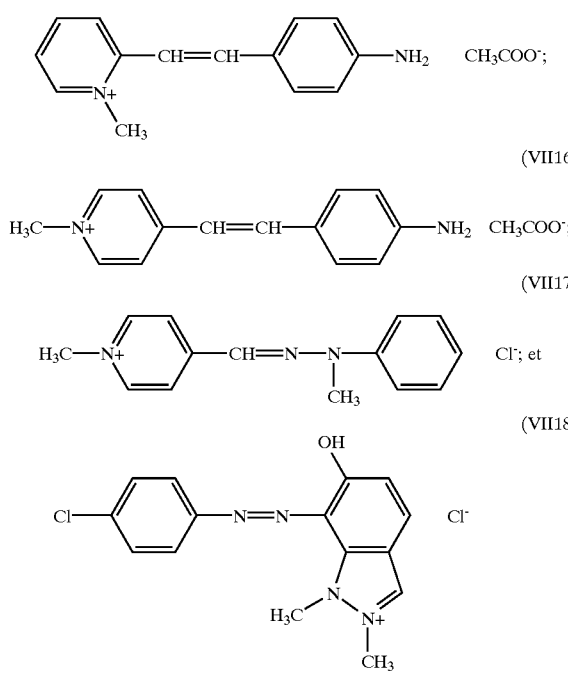

(VII14)

(VII15)

(VII16)

(VII17)

(VII18)

Among the compounds with structures (VII1) to (VII18) especially preferred are compounds with structures (VII4), (VII5) and (VII13).

Among the direct cationic colors with formula (VII'), especially preferred are compounds with the following structures (VII'1) to (VII'3):

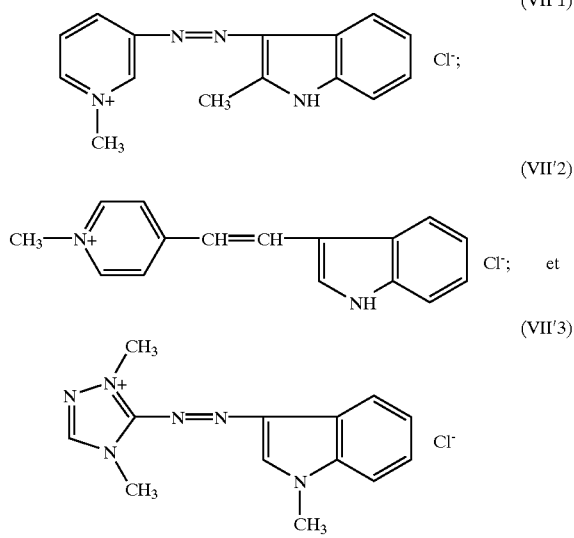

(VII'1)

(VII'2)

(VII'3)

The direct cationic colors may be applied in amounts from 0,001 to 10 wt-% based on the total amount of the dyeing composition, preferably from 0,05 to 5 wt-%.

In a general way the acid addition salts that can be used in the colouring compositions of the invention (precursers and couplers) are especially chosen among chlorhydrates, bromhydrates, sulfates and tartrates, lactates and acetates.

The proper environment for the colouring (or support) of the ready-to-use colouring composition corresponding to the invention is generally composed of water or a mixture of water and at least an organic solvent to dissolve the components that are not sufficiently soluble in water. As an example of an organic solvent one can mention $C_1$–$C_4$ alcanols, such as ethanol and isopropanol as well as aromatic alcohols like benzyl alcohol, and analogue products and their mixtures.

The solvents can be present in quantities preferably between 1 and 40% of the total weight of the colouring composition and rather between 5 and 30% of the weight.

The pH of the ready-to-use composition corresponding to the invention is chosen in a way that ensures a sufficient enzymatic activity of the laccase. The pH generally lies between 4 and 11 and preferably between 6 and about 9.

The ready-to-use colouring composition corresponding to the invention can also contain different additives typically used in hair colouring compositions, such as anionic, cationic, non-ionic, amphoteric or zwitterionic tensio-active agents or their mixtures, polymers, thickening agents, antioxidants, different laccase enzymes used in correspondance with the invention, such as peroxydases or oxidoreductases with 2 electrons, penetration agents, sequestrant agents, perfumes, buffers, dispersion agents, filmogene agents, filtration agents, vitamins, preservation agents and opacity agents.

Of course a person skilled in the art will be careful to choose the possible complementary components in a way that the advantageous properties of the ready-to-use colouring composition corresponding to the invention are not, or not substantially, changed by the foreseen adjunctions.

The ready-to-use colouring composition corresponding to the invention can have different forms, such as liquids, creams, gels, maybe pressurized, or any other form that is appropriate for colouring keratinous fibres, and especially human hair. In this case the oxidation colour or colours and the laccase or laccases are present in the same ready-to-use composition, and consequently the mentioned composition must be free of gaseous oxygene in order to avoid any premature oxidation of the oxidation colour or colours.

The invention has also as an objective a colouring procedure of keratinous fibres and especially human keratinous fibres such as hair, implementing the ready-to-use colouring comopsition such as defined above.

According to this procedure, at least one ready-to-use colouring composition such as defined earlier is applied to the fibres, for a time that is sufficient to develop the desired coloration, whereafter the fibres are rinsed, if necessary washed with a shampoo, rinsed again, and dried.

The time necessary for developing the coloration of the keratinous fibres generally lies between 3 and 60 minutes and more precisely between 5 and 40 minutes.

According to a special realisation form of the invention the procedure includes a preliminary stage consisting in stocking in separate form, on one side, a composition (A) comprising, in an environment appropriate for colouring, at least one oxidation colour, at least one direct cationic colour and, on the other side, a composition (B) including, in an environment appropriate for colouring, at least one enzyme of the laccase type, than proceeding with the mixing of these at the moment of use before the mixture is applied to the keratinous fibres.

Another object of the invention is a device with more compartments or a colouring kit or any other container system with more compartments, of which a first compartment contains the composition (A) as defined above and a second compartment contains the composition (B) as defined above. These devices can be equipped with means permitting to apply the desired mixture to the hair, as the devices described in the FR-2 586 913.

By adding small amounts (i.e., 0.001–1%, preferably 0.01–0.5%) of a hydrogen peroxide source along with at least one oxidoreductase and one or more mediators, the efficiency of dyeing increases substantially, while no significant damage to the hair is observed. Furthermore, inclusion of a hydrogen peroxide source aids in re-formation of hair cross links after initial reduction of cross links in a hair straightening process. Consequently, the invention provides a convenient method for combining hair straightening with permanent hair dyeing such that the resulting hair damage is not significant.

According to the present invention the dyeing of the hair comprises contacting said hair with a dyeing composition comprising at least one oxidoreductase, at least one mediator, and at least one chemical oxidizing agent in an amount equivalent to 0.001–1% hydrogen peroxide calculated by weight of the dyeing composition.

At least one means in the context of the present invention that e.g. the mediators i.e. precursors, modifiers/couplers and enhancing agents may be combined such that more Precursors, modifiers/coupler and enhancing agents may be used together.

MATERIALS AND METHODS

Materials:
  Enzyme
    Laccase solution: *Myceliophthora therirophila laccase* (*MtL*) described in WO 95/33836 (Novo Nordisk), stock solution, 1170 LAMU/mL
    Peroxidase solution: concentrated enzyme solution (6,092 PoxU/mL), from Coprinus sp.

Methods:
  Cysteic Acid Assay
  Cysteic acid quantification is frequently used to assess hair damage. This value can be determined using routine amino acid analysis techniques well-known in the art.
  Thiol Assay
  Thiol content is frequently used to assess the level of fixation of hair. Higher values for thiol content indicate that hair is in a reduced state; i.e., there are more mercaptan groups than normal. Thiol values are determined using a polarographic method. Keratin samples are treated with a known excess of methyl mercuric chloride and the amount of reagent that reacts with the hair is estimated by polarography.
  Determination POXU
  One POXU is the amount of enzyme that catalyzes the conversion of 1 µmol of $H_2O_2$ per minute in a system in which ABTS (2,2'azinobis[3-ethylbenzothiazoline-6-sulfonic acid]) is oxidized.
  Determination of Laccase Activity (LAMU)
  The LAMU method is used for determining the activity of *Myceliophthora thermophila laccase*. 1 laccase unit (LUAU) is the amount of enzyme which catalyses the conversion of 1.0 micro mole syringaldazine per minute under the following analytical conditions. Further details on how to determine LAMU can be found in WO 98/40471 (see pages 18 to 20) (Novo Nordisk)

EXAMPLES

Example 1

Fourteen samples of African-American hair (obtained from De Meo Brothers, Inc., each sample contained about 1 g hair) were prepared by fusing the root ends with adhesive. Half of the samples were subjected to blank control treatments, while the other half were subjected to the chemical reducing agent of a commercial straightening (Revlon Fabulaxer®, calcium hydroxide based) treatment. After rinsing, samples were subjected to one of several different oxidative secondary treatments, as described in the table below.

| Sample | Pre-treat | Catalyst System |
|--------|-----------|-----------------|
| 1 | Relax | A |
| 2 | relax | B |
| 3 | relax | C |
| 4 | relax | D |
| 5 | relax | E |
| 6 | relax | F |
| 7 | blank | A |
| 8 | blank | B |
| 9 | blank | C |
| 10 | blank | D |
| 11 | blank | E |
| 12 | blank | F |

Relaxer Treatment:
  Blank: Control sample, immerse in water
  Relaxer: Commercial hair relaxer gel (Revlon Fabulaxer®, calcium hydroxide-based).
Mediators
  Mediator Solution: 0.6 g p-phenylenediamine, 0.6 g 3-aminophenol, 0.6 g 4-amino-phenol, dissolved in 18 mL acetone. One mL of this solution was added for all oxidative treatments.
Catalyst Systems
  Catalyst System A, "Laccase Low": 15 µL 50% peroxide solution (0.015% $H_2O_2$ in final solution), 250 µL laccase solution, 50 mL buffer.
  Catalyst System B, "Laccase High": 50 µL 50% peroxide solution (0.05% $H_2O_2$ in final solution), 500 µL laccase solution, 50 mL buffer
  Catalyst System C, "Peroxidase Low": 15 µL 50% peroxide solution (0.015% $H_2O_2$ in final solution), 100 µL peroxidase solution, 50 mL buffer
  Catalyst System D, "Peroxidase High": 100 µL 50% peroxide solution (0.1% $H_2O_2$ in final solution), 300 µL peroxidase solution, 50 mL buffer
  Catalyst System E, "Peroxide Low": 2.0 mL 50% peroxide solution (2% $H_2O_2$ in final solution), no enzymes, 50 mL buffer
  Catalyst System F, "Peroxide High": 5.0 mL 50% peroxide solution (5% $H_2O_2$ in final solution), no enzymes, 50 mL buffer.
Enzyme and Buffer Solutions
  Laccase solution: *Myceliophthora thermophila laccase* (*MtL*) described in WO 95/33836 (Novo Nordisk), stock solution, 1170 LAMU/mL
  Peroxidase solution: concentrated enzyme solution (6,092 POXU/mL), from Coprinus sp.

pH 8 Buffer Solution: 0.05 M Britton and Robinson buffer (B-R buffer), pH 8.

First (reduction) Treatments: The reduction lotion was applied to the samples which were then combed straight and pressed onto a paper towel for a period of 25 minutes.

Hair was rinsed in running water, swirled in a pH 6 sodium acetate buffer, and rinsed again under additional running water.

Oxidative/Dye Treatments: Components of the catalyst systems described above were added to beakers, followed by hair and mediator solution (1 mL). The hair was swirled briefly, then was removed after 5 minutes exposure to solution, and placed on a paper towel. After 20 minutes, the hair samples were rinsed thoroughly.

After the hair was dried, a color reading was obtained on a spectrophotometer (MacBeth ColorEye®). Hair was washed, dried, and analyzed again for color. This process was repeated again, this time after washing for an hour. Hair washes were conducted in jars using 200 mL shampoo solution (made up of 10 mL Pantene Pro-V® shampoo in 2 L water) in an environmental shaker at 45° C., with moderate agitation (100 rpm), for 5 minutes, unless otherwise specified.

Color measurements were obtained by wrapping hair around a small piece of cardboard to obtain a wound spool hiding the cardboard packing, then analyzing the color spectrophotometrically. Color loss analysis was based on DE* values. Hair samples were compared to calibrated reference standards during each color measurement cycle, and thus the absolute L*a*b* values recorded in the data table may not correspond exactly with the values calculated for color loss. In the data table below, "color less"= $(DE^*_{wash}/DE^*_{unwashed})$, a measure of the relative loss of color washing. Results are shown in the table below.

| Treatment | Sample | # Wash | L* | a* | b* | DE* | Color Loss |
|---|---|---|---|---|---|---|---|
| None | Std. | 0 | 19.34 | 1.91 | 4.32 | 1.10 | |
| | Std. | 1 | 19.34 | 1.94 | 4.14 | 1.10 | |
| | Std. | 2 | 19.77 | 2.61 | 3.36 | 1.10 | |
| Straightened Hair, samples 1–6 | | | | | | | |
| Laccase, low conc. | 1 | 0 | 16.48 | 0.77 | 1.10 | 4.46 | |
| | 1 | 1 | 17.56 | 0.76 | 1.22 | 3.62 | 19 |
| | 1 | 2 | 18.02 | 1.98 | 1.83 | 2.41 | 46 |
| Laccase, high conc. | 2 | 0 | 14.70 | 0.28 | 0.16 | 6.45 | |
| | 2 | 1 | 17.91 | 0.39 | 0.68 | 4.06 | 37 |
| | 2 | 2 | 17.68 | 1.04 | 0.57 | 3.82 | 41 |
| Peroxidase, low | 3 | 0 | 15.05 | 0.47 | 0.34 | 6.03 | |
| | 3 | 1 | 16.85 | 0.53 | 0.60 | 4.55 | 25 |
| | 3 | 2 | 17.09 | 1.04 | 0.45 | 4.26 | 29 |
| Peroxidase, high | 4 | 0 | 15.39 | 0.47 | 0.45 | 5.72 | |
| | 4 | 1 | 17.15 | 0.47 | 0.87 | 4.20 | 26 |
| | 4 | 2 | 18.02 | 1.46 | 1.11 | 3.07 | 46 |
| Peroxide, low | 5 | 0 | 15.73 | 0.65 | 0.78 | 5.21 | |
| | 5 | 1 | 17.31 | 0.88 | 1.37 | 3.60 | 31 |
| | 5 | 2 | 17.27 | 1.32 | 0.91 | 3.73 | 28 |
| Peroxide, high | 6 | 0 | 16.26 | 0.79 | 0.99 | 4.67 | |
| | 6 | 1 | 16.92 | 0.94 | 1.37 | 3.81 | 18 |
| | 6 | 2 | 17.65 | 1.67 | 1.54 | 2.95 | 37 |
| Untreated Hair, samples 7–12 | | | | | | | |
| Laccase, low conc. | 7 | 0 | 16.20 | 1.40 | 2.72 | 3.57 | |
| | 7 | 1 | 17.64 | 1.08 | 2.06 | 2.82 | 21 |
| | 7 | 2 | 17.76 | 2.05 | 2.18 | 2.40 | 33 |
| Laccase, high conc. | 8 | 0 | 14.77 | 0.82 | 1.38 | 5.54 | |
| | 8 | 1 | 17.03 | 1.04 | 2.07 | 3.23 | 42 |
| | 8 | 2 | 17.22 | 1.70 | 1.81 | 3.11 | 44 |
| Peroxidase, low | 9 | 0 | 14.25 | 1.17 | 2.11 | 5.60 | |
| | 9 | 1 | 17.98 | 1.30 | 2.75 | 2.05 | 63 |
| | 9 | 2 | 18.68 | 2.20 | 2.59 | 1.40 | 75 |
| Peroxidase, high | 10 | 0 | 14.89 | 0.94 | 1.69 | 5.27 | |
| | 10 | 1 | 17.86 | 1.08 | 2.21 | 2.58 | 51 |
| | 10 | 2 | 18.87 | 2.16 | 2.41 | 1.39 | 74 |
| Peroxide, low | 11 | 0 | 14.92 | 0.87 | 1.42 | 5.39 | |
| | 11 | 1 | 17.22 | 0.94 | 1.55 | 3.50 | 35 |
| | 11 | 2 | 17.79 | 1.66 | 1.65 | 2.79 | 48 |
| Peroxide, high | 12 | 0 | 14.50 | 0.87 | 1.42 | 5.75 | |
| | 12 | 1 | 16.79 | 0.87 | 1.39 | 3.90 | 32 |
| | 12 | 2 | 17.83 | 1.78 | 1.73 | 2.67 | 53 |

In summary, dyeing of chemically straightened hair is more efficient than dyeing of untreated hair, giving stronger color. Furthermore, for most treatments, the percentage of color remaining on the hair after dyeing was significantly higher for samples receiving an initial straightening treatment than for samples receiving an initial blank treatment. For all samples, the final color after multiple washes was darker on hair that had been chemically straightened.

Example 2

Twelves of African-American hair (obtained from De Moe Brothers, Inc., each sample contained about 1.00 g hair) were prepared by fusing the root ends with adhesive. Most of the samples were subjected to chemical reduction (Revlon Fabulaxer®) and mechanical straightening, while two samples were given a blank control treatment. After rinsing, samples were subjected to one of several different oxidative secondary treatments, as described in the table below.

| Sample | Pre-treat | Mediators | Catalyst |
|---|---|---|---|
| 1 | Relax | y | A |
| 2 | relax | y | B |
| 3 | relax | y | C |
| 4 | relax | y | D |
| 5 | relax | N | E |
| 6 | relax | y | F |
| 7 | relax | y | G |
| 8 | relax | y | H |
| 9 | relax | y | I |
| 10 | relax | y | G |
| 11 | blank | y | G |
| 12 | blank | y | C |

Relaxer Treatment:
  Blank: Control sample, immerse in water
  Relaxer: Commercial hair relaxer gel (Revlon Fabulaxer, calcium hydroxide-based).
  Mediators
  Mediator Solution: 0.6 g p-phenylenediamine, 0.6 g 3-aminophenol, 0.6 g 4-amino-phenol, dissolved in 18 mL acetone. One mL of this solution was added for all oxidative treatments.
Catalyst Systems
  Catalyst System A: 10 µL 50% peroxide solution (0.01% $H_2O_2$ in final solution), 100 µL laccase solution, 50 mL buffer
  Catalyst System B: 10 µL 50% peroxide solution (0.01% $H_2O$ in final solution), 400 µL laccase solution, 50 mL buffer Catalyst System C: 50 μL 50% peroxide solution (0.05% $H_2O_2$ in final solution), 100 μL laccase solution, 50 mL buffer Catalyst System D: 50 μL 50% peroxide solution (0.05% $H_2O_2$ in final solution), 400 μL laccase solution, 50 mL buffer Catalyst System E: 6.0 mL 50% peroxide solution (6% $H_2O_2$ in final solution), no enzymes, no-mediators, 50 mL buffer Catalyst System F: 10 mL 50% peroxide solution (10% $H_2O_2$ in final solution), 50 μL peroxidase solution, 50 mL buffer Catalyst System G: 10 μL 50% peroxide solution (0.01% $H_2O_2$ in final solution), 150 μL peroxidase solution, 50 mL buffer Catalyst System H: 10 μL 50% peroxide solution (0.01% $H_2O_2$ in final solution), 450 μL peroxidase solution, 50 mL buffer Catalyst System I: 30 μL 50% peroxide solution (0.03% $H_2O_2$ in final solution), 150 μL peroxidase solution, 50 mL buffer.

Enzyme and Buffer Solutions

Laccase solution: *Myceliophthora thermophila laccase* (*MtL*) described in WO 95/33836 (Novo Nordisk), stock solution, 1170 LAMU/mL Peroxidase solution: concentrated enzyme solution (6,092 POXU/mL), from Coprinus sp.

pH 8 Buffer Solution: 0.05 M Britton and Robinson buffer (B-R buffer), pH 8.

First (reduction) Treatments: The reduction lotion was applied to the samples which were then combed straight and pressed onto a paper towel for a period of 25 minutes. Hair was rinsed in running water, swirled in acidic buffer, and rinsed again under additional running water.

Oxidative/Dye Treatments: The components of the catalyst systems described above were added to beakers, followed by hair and mediator solution (1 mL). The hair was swirled briefly, then removed after 5 minutes exposure to solution, and placed on a paper towel. After 20 minutes, the hair samples were rinsed thoroughly.

After the hair was dried, a color reading was obtained on a is spectrophotometer. Color measurements were obtained as described in Example 1.

Hair was washed, dried, and analyzed again for color. This process was repeated ten times. Hair washes were conducted in jars using 200 mL shampoo solution (made up of 10 mL Pantene ProV® shampoo in 2 L water) in an environmental shaker at 45° C., with moderate agitation (100 rpm), for 5 minutes, unless otherwise specified.

Results are shown in FIG. 1. Hair was dyed black.

Relative to dyed samples of hair in its fully oxidized form, straightened hair was dyed a darker color, and had superior washfastness, and was also straight rather than curly.

Example 3

Eight samples of African-American hair (obtained from De Meo Brothers, Inc., each sample contained about 1.00 g hair) were prepared by fusing the root ends with adhesive. Some of the samples were subjected to commercial chemical reduction (relaxer, guanidinium hydroxide-based) treatments in which the hair was mechanically straightened, while others were given a blank control treatment consisting of immersion in water. After rinsing, samples were subjected to one of several different oxidative secondary treatments, with addition of the designated catalysts and mediators (see table in FIG. 1).

Relaxer Treatment:

Blank: Control sample, immerse in water

Relaxer: Commercial hair relaxer gel, (guanidinium hydroxidebased)

Mediator Solution: 0.6 g p-phenylenediamine, 0.6 g 3-aminophenol, 0.6 g 4-amino-phenol, dissolved in 18 mL acetone, of which 1 mL was added in designated treatments (designated by a "Y" in the mediator column of table).

Catalyst Systems

Catalyst System A: 15 μL 50% peroxide solution (0.015% $H_2O_2$ in final solution), 250 mL laccase solution, 50 mL buffer Catalyst System B: 15 μL 50% peroxide solution peroxide solution (0.015% $H_2O_2$ in final solution), 100 μL peroxidase solution, 50 mL buffer Catalyst System C: 100 μL 50% peroxide solution peroxide solution (0.1% $H_2O_2$ in final solution), 300 μL peroxidase solution, 50 mL buffer Catalyst System D: 2.0 mL 50% peroxide solution peroxide solution (2% $H_2O_2$ in final solution), no enzymes, 50 mL buffer Catalyst System E: Commercial Neutralization Solution (for permed hair) from Rave.

Catalyst System F: Water blank

Enzyme and Buffer Solutions

Laccase solution: *Myceliophthora thermophila laccase* (*MtL*) described in WO 95/33836 (Novo Nordisk), stock solution, 1170 LAMU/mL Peroxidase solution: concentrated enzyme solution (6,092 POXU/mL), from Coprinus sp.

pH 5.5 Buffer Solution: 0.05 M Sodium acetate buffer, pH 5.5.

First (reduction) Treatments: The reduction lotion was applied to the samples which were then combed straight and pasted onto a paper towel for a period of 25 minutes. Hair was rinsed in running water, swirled in acidic buffer, and rinsed again under additional running water.

Oxidative/Dye Treatments: The components of the catalyst systems described above were added to beakers, followed by hair and mediator solution (1 mL). The hair was swirled briefly, then removed after 5 minutes exposure to solution, and placed on a paper towel. After 20 minutes, the hair samples were rinsed thoroughly

TABLE

Hair Damage and Fixation

| Sample | Pre-treat | Mediators (Y/N) | Catalyst | Thiol Content (mmol/g hair) | Cysteic Acid (mol-%) |
|---|---|---|---|---|---|
| 1 | Blank | N | E | 41 | 0.75 |
| 2 | Blank | N | F | 44 | 0.66 |
| 3 | Blank | Y | A | 42 | 0.59 |
| 4 | Relax | Y | A | 69 | 0.56 |
| 5 | Relax | Y | B | 66 | 0.54 |
| 6 | Relax | Y | C | 58 | 0.66 |
| 7 | Relax | Y | D | 43 | 0.94 |
| 8 | Relax | N | E | 46 | 1.00 |

Cysteic acid quantification is frequently used to assess hair damage. Lower values are preferred. In the table above, it can be seen that enzyme-mediated dyeing, when employed after a chemical relaxation step, caused very little damage to the air (samples 4, 5, and 6), essentially indistinguishable from treated hair (sample 2).

Thiol content is often used to assess hair fixation, i.e., re-formation of cross links in hair. In general, lower numbers are indicative of superior fixation. After a permanent waving or straightening treatment, and without an aggressive oxidation step (i.e., relying solely on air oxidation), thiol values were observed in the range 70–150, depending on the reducing treatment. In the above table, it is apparent that thiol contents were low for all samples, not as low for samples fixated enzymatically (samples 4–6) as for those fixated via hydrogen peroxide oxidation (samples 7 and 8), but lower than for samples of reduced hair not subjected to an aggressive oxidative treatment (as is frequently the case for commercial straightening products).

Example 4

Twelve samples of African-American hair (obtained from De Meo Brothers, Inc., each sample contained about 1.00 g hair) were prepared by fusing the root ends with adhesive. All of the samples were subjected to chemical reduction (Revlon Fabulaxer®) and mechanical straightening. After rinsing, samples were subjected to one of several different oxidative secondary treatments.

Straightening Treatment:
 Commercial hair relaxer gel (Revlon Fabulaxer®).
Mediators
 Mediator Solution: 0.6 g p-phenylenediamine, 0.6 g 3-aminophenol, 0.6 g 4-amino-phenol, dissolved in 18 mL acetone. One mL of this solution was added for all oxidative treatments.
Catalyst Systems
 Catalyst System A: 0 mL hydrogen peroxide, (0% $H_2O_2$ in final solution), 400 µL peroxidase solution, 50 mL buffer
 Catalyst System B: 10 µL 50% peroxide solution (0.01% $H_2O_2$ in final solution), 400 µL peroxidase solution, 50 mL buffer
 Catalyst System C: 20 µL 50% peroxide solution (0.02% $H_2O_2$ in final solution), 400 µL peroxidase solution, 50 mL buffer
 Catalyst System D: 30 µL 50% peroxide solution (0.03% $H_2O_2$ in final solution), 400 µL peroxidase solution, 50 mL buffer
 Catalyst System E: 40 µL 50% peroxide solution (0.04% $H_2O_2$ in final solution), 400 µL peroxidase solution, 50 mL buffer
 1Catalyst System F: 50 µL 50% peroxide solution (0. 05% $H_2O_2$ in final solution), 400 µL peroxidase solution, 50 mL buffer
Enzyme and Buffer Solutions
 Laccase solution: *Myceliophthora thermophila laccase* (*MtL*) described in WO 95/33836 (Novo Nordisk), stock solution, 1170 LAMU/mL
 Peroxidase solution: concentrated enzyme solution (6,092 POXU/mL), from *Coprinus sp.*
 pH 8 Buffer Solution: 0.05 M Britton and Robinson buffer (B-R buffer), pH 8.

First (reduction) Treatments: The reduction lotion was applied to the samples which were then combed straight and pressed onto a paper towel for a period of 25 minutes. Hair was rinsed in running water, swirled in acidic buffer, and rinsed again under additional running water.

Oxidative/Dye Treatments: The components of the catalyst systems described above were added to beakers, followed by hair and mediator solution (1 mL). The hair was swirled briefly, then removed after 5 minutes exposure to solution, and placed on a paper towel. After 20 minutes, the hair samples were rinsed thoroughly.

After the hair was dried, a color reading was obtained on a spectrophotometer. Color measurements were obtained as described in Example 1.

Hair was washed, dried, and analyzed again for color. This process was repeated ten times. Hair washes were conducted in jars using 200 mL shampoo solution (made up of 10 mL Pantene Pro-V® shampoo in 2 L water) in an environmental shaker at 45° C, with moderate agitation (100 rpm), for 5 minutes, unless otherwise specified.

Results are shown in the proceeding table, which indicates hair color after ten wash cycles. Hair was dyed black.

| Sample | Catalyst | L* | a* | b* | dE* |
|---|---|---|---|---|---|
| 1 | A (0) | 18.88 | 2.57 | 2.57 | 1.01 |
| 2 | A (0) | 18.23 | 2.55 | 2.57 | 1.54 |
| 3 | B (10) | 16.94 | 0.93 | 0.31 | 4.38 |
| 4 | B (10) | 16.55 | 0.86 | 0.25 | 4.69 |
| 5 | C (20) | 16.78 | 0.75 | 0.11 | 4.69 |
| 6 | C (20) | 16.46 | 0.61 | 0.06 | 4.98 |
| 7 | D (30) | 16.47 | 0.60 | -0.02 | 5.02 |
| 8 | D (30) | 16.42 | 0.64 | 0.05 | 4.99 |
| 9 | E (40) | 15.99 | 0.87 | 0.14 | 5.13 |
| 10 | E (40) | 16.07 | 0.77 | 0.10 | 5.15 |
| 11 | F (50) | 16.10 | 0.99 | 0.28 | 4.93 |
| 12 | F (50) | 16.61 | 0.83 | 0.09 | 4.78 |

Note:
In the column headed catalyst, values in parentheses refer to the amount (in µL) of added hydrogen peroxide.
Values for dE* are calculated relative to an untreated wisp of hair with values for L*, a*, and b* of 19.57, 2.80, and 3.27, respectively.

The results indicate that dyeing performance is enhanced for samples exposed to $H_2O_2$ during the dyeing process relative to samples that were not exposed to $H_2O_2$ (samples 1 and 2).

Example 5

Eight samples of blande hair (obtained from De Meo Brothers, Inc., each sample contained about 1.0 g hair) were prepared by fusing the root ends with adhesive. Half of the samples were subjected to a blank pre-treatment step consisting of immersion in water, while the other half were treated with a commercial hair relaxing gel (Revlon Fabulaxer®). After rinsing, samples were subjected to an enzyme-mediated dyeing step, using either a laccase or a peroxidase.

Mediators
 Mediator Solution: 0.9 g p-phenylenediamine, 0.9 g 1-naphthol dissolved in 18 mL acetone
Catalysts
 Catalyst System A: 30 µL 50% peroxide solution, 500 µL laccase solution, 50 mL buffer
 Catalyst System B: 30 µL 50% peroxide solution, 400 µL peroxidase solution, 50 mL buffer
Enzyme and Buffer Solutions
 Laccase solution: *MtL*(*Myceliophthora thermophila laccase*), stock solution, 1170 LamU/mL
 Peroxidase solution: concentrated enzyme solution (6,092 PoxU/mL) from *Coprinus Sp.*
 pH 8 Buffer Solution: 0.05 M Britton-Robinson buffer, pH 8.0.

First (reduction) Treatments: The reduction lotion was applied to the samples which were then combed straight and pressed onto a paper towel for a period of 25 minutes. Hair was rinsed in running water, swirled in acidic buffer, and rinsed again under additional running water.

Oxidative/Dye Treatments: The components of the catalyst systems described above were added to beakers, followed by hair and mediator solution (1 mL). The hair was swirled briefly, then removed after 5 minutes exposure to solution, and placed on a paper towel. After 20 minutes, the hair samples were rinsed thoroughly.

After the hair was dried, a color reading was obtained on a spectrophotometer. Color measurements were obtained as described in example 1.

Hair was washed, dried, and analyzed again for color. This process was repeated ten times. Hair washes were conducted in jars using 200 mL shampoo solution (made up of 10 mL Pantene Pro-V® shampoo in 2 L water) in an environmental shaker at 45° C, with moderate agitation (100 rpm), for 5 minutes, unless otherwise specified.

Results are shown in the following table, which indicates hair color after zero and ten wash cycles. Hair was dyed a dark color. The standard blonde sample (untreated, unwashed) against which the tested samples were compared had $L^*$, $a^*$, and $B^*$ values of 35.89, 6.48, and 14.46, respectively, when measured at the time of the first reading (when samples were unwashed), and 36.45, 6.38, and 14.37, respectively, when measured prior to analyzing sample tresses after ten washes.

Catalysts

Catalyst System A: 50 µL 50% peroxide solution, 500 µL laccase solution, 50 mL buffer Catalyst System B: 50 µL 50% peroxide solution, 400 µL peroxidase solution, 50 mL buffer Enzyme and Buffer Solutions Laccase solution: MtL(*Myceliophthora thermophila laccase*), stock solution, 1170 LamU/mL Peroxidase solution: concentrated enzyme solution (6,092 PoxU/mL) from Coprinus Sp.

pH 8 Buffer Solution: 0.05 M Britton-Robinson buffer, pH 8.0.

First (reduction) Treatments:

Blank treatments: Hair was immersed in water for 30 minutes, then removed prior to dyeing Relax (48) treatments: The reduction lotion of a commercial hair relaxer was applied to hair samples, which were then combed straight and pressed onto a paper towel for a period of minutes. Hair was rinsed in running water, then treated with the accompanying commercial neutralizing lotion. After rinsing, hair was treated with the accompanying commercial conditioning shampoo, then allowed to stand for 24 hours. Hair samples were washed according to the protocol given below, then allowed to stand another 24 hours. Hair was rinsed prior to dyeing.

Relax (0) treatments: The reduction lotion of a commercial hair relaxer was applied to hair samples, which were

| | | | Unwashed | | | | 10 washes | | | |
|---|---|---|---|---|---|---|---|---|---|---|
| Sample | Pre-treat | Enzyme | $L^*$ | $a^*$ | $b^*$ | $dE^*$ | $L^*$ | $a^*$ | $b^*$ | $dE^*$ |
| 1 | Relax | laccase | 21.34 | 2.56 | −0.57 | 21.28 | 26.49 | 2.61 | 2.83 | 15.71 |
| 2 | relax | laccase | 21.94 | 3.15 | −0.05 | 20.40 | 25.92 | 2.99 | 3.04 | 15.84 |
| 3 | relax | peroxidase | 22.64 | 2.05 | −0.73 | 20.63 | 26.92 | 3.09 | 3.62 | 14.74 |
| 4 | relax | peroxidase | 21.58 | 2.71 | −0.31 | 20.90 | 25.68 | 2.33 | 2.50 | 16.54 |
| 5 | blank | laccase | 22.80 | 4.01 | 0.53 | 19.27 | 28.17 | 4.61 | 5.33 | 12.39 |
| 6 | blank | laccase | 24.41 | 4.22 | 0.15 | 18.48 | 28.86 | 4.72 | 5.89 | 11.50 |
| 7 | blank | peroxidase | 23.40 | 4.37 | 1.64 | 18.02 | 29.19 | 4.89 | 7.38 | 10.19 |
| 8 | blank | peroxidase | 24.59 | 4.45 | 2.60 | 16.50 | 28.75 | 5.14 | 7.09 | 10.68 |

These results indicate that the efficiency of dyeing of blonde hair was improved when dyeing was performed on chemically straightened hair relative to untreated hair. The initial color was stronger, and the washfastness was also superior.

Example 6

Twelve samples of African hair (obtained from De Meo Brothers, Inc., each sample contained about 1.0 g hair) were prepared by fusing the root ends with adhesive. Immediately prior to dyeing, four of the samples were subjected to a blank pre-treatment step consisting of immersion in water, while another four were treated with a commercial hair relaxing gel from Revlon, then rinsed. The remaining four samples had been subjected to the hair straightening process 48 hours previously, including the commercial neutralization step and post-treatment conditioner. They were washed 24 hours later with shampoo, and were rinsed in water prior to dyeing. After rinsing, samples were subjected to an enzyme-mediated dyeing step, using either a laccase or a peroxidase.

Mediators

Mediator Solution: 0.6 g p-phenylenediamine, 0.6 g 3-inophenol, 0.6 g 4-amino-phenol, dissolved in 18 mL acetone.

then combed straight and pressed onto a paper towel for a period of 20 minutes. Hair was rinsed in running water, swirled in acidic buffer, and rinsed again under additional running water.

Oxidative/Dye Treatments: The components of the catalyst systems described above were added to beakers, followed by hair and mediator solution (1 mL). The hair was swirled briefly, then removed after 5 minutes exposure to solution, and placed on a paper towel. After 20 minutes, the hair samples were rinsed thoroughly.

After the hair was dried, a color reading was obtained on a spectrophotometer. Color measurements were obtained as described in Example 1.

Hair was washed, dried, and analyzed again for color. This process was repeated ten times. Hair washes were conducted in jars using 200 mL shampoo solution (made up of 10 mL Pantene Pro-V® shampoo in 2 L water) in an environmental shaker at 45° C, with moderate agitation (100 rpm), for 5 minutes, unless otherwise specified.

Results are shown in the following table, which indicates hair color after zero and ten wash cycles. Hair was dyed a black color. The standard African hair sample (untreated, unwashed) against which the tested samples were compared had $L^*$, $a^*$, and $B^*$ values of 19.15, 2.75, and 3.47, respectively, when measured at the time of the first reading (when samples were unwashed), and 19.23, 2.38, and 2.76, respectively, when measured prior to calorimetric analysis of the hair tresses after ten washes.

| Sample | Pre-treat | Enzyme | Unwashed | | | | 10 washes | | | |
|---|---|---|---|---|---|---|---|---|---|---|
| | | | L* | a* | b* | dE* | L* | a* | b* | dE* |
| 1 | blank | laccase | 15.36 | 1.54 | 1.66 | 4.38 | 16.98 | 1.69 | 1.57 | 2.64 |
| 2 | blank | laccase | 15.53 | 1.54 | 1.63 | 4.24 | 16.68 | 1.63 | 1.54 | 2.93 |
| 3 | blank | peroxidase | 15.11 | 1.83 | 1.82 | 4.47 | 16.75 | 1.83 | 1.86 | 2.70 |
| 4 | blank | peroxidase | 15.41 | 1.90 | 1.93 | 4.14 | 16.71 | 1.96 | 1.96 | 2.68 |
| 5 | relax (48) | laccase | 15.95 | 0.99 | 0.69 | 4.60 | 16.42 | 1.33 | 0.92 | 3.53 |
| 6 | relax (48) | laccase | 16.12 | 0.78 | 0.48 | 4.69 | 16.18 | 1.31 | 0.89 | 3.73 |
| 7 | relax (48) | peroxidase | 16.01 | 0.70 | 0.40 | 4.85 | 16.51 | 1.24 | 0.84 | 3.53 |
| 8 | relax (48) | peroxidase | 16.15 | 0.77 | 0.51 | 4.66 | 16.58 | 1.25 | 0.75 | 3.52 |
| 9 | relax (0) | laccase | 16.58 | 0.72 | 0.07 | 4.73 | 15.86 | 1.01 | 0.39 | 4.34 |
| 10 | relax (0) | laccase | 16.76 | 0.57 | −0.12 | 4.83 | 15.88 | 1.22 | 0.47 | 4.22 |
| 11 | relax (0) | peroxidase | 16.54 | 0.44 | −0.21 | 5.08 | 15.44 | 0.92 | 0.17 | 4.82 |
| 12 | relax (0) | peroxidase | 15.85 | 0.90 | 0.40 | 4.88 | 16.47 | 1.68 | 1.24 | 3.23 |

These results show that the quality of enzyme-mediated dyeing was better on hair relaxed immediately prior to dyeing than on hair relaxed 48 hours previously, which in turn was superior to dyeing of untreated hair.

What is claimed is:

1. A method for treating reduced hair comprising contacting said hair with a dyeing composition comprising at least one laccase, at least one mediator, and at least one chemical oxidizing agent that produces hydrogen peroxide in an amount equivalent to 0.001–1% calculated by weight of the dyeing composition.

2. The method of claim 1, wherein said hair has been reduced using a hydroxide-based chemical reducing agent.

3. The method of claim 2, wherein the hair has been chemically reduced using sodium hydroxide, calcium hydroxide, or guanidinium hydroxide.

4. A method of claim 1, wherein the laccase is derived from Myceliophthora sp.

5. The method of claim 4, wherein the laccase is derived from M. thermophila.

6. The method of claim 1, wherein the mediator(s) is(are) selected from the group consisting of diamines, aminophenols, aminonaphthols and phenols and combinations thereof.

7. The method of claim 1, wherein the mediator(s) is(are) selected from the group consisting of 2,2'-azino-bis(3-ethylbenzothiazoline-6-sulfonate (ABTS), 6-hydroxy-2-naphthoic acid, 7-methoxy-2-naphthol, 7-amino-2-naphthalene sulfonic acid, 5-amino-2-naphthalene sulfonic acid, 1,5-diaminonaphthalene, 7-hydroxy-1,2-naphthimidazole, 10-methylphenothiazine, 10-phenothiazine-propionic acid (PPT), N-hydroxysuccinimide-10-phenothiazine-proptonate, benzidine, 3,3'-dimethylbenzidine, 3,3'-dimethoxybenzidine, 3,3',5,5'-tetramethylbenzidine, 4'-hydroxybiphenylcarboxylic acid, 4-amino-4'-methoxystilbene, 4,4'-diaminostilbene-2,2'-disulfonic acid, 4,4'-diaminodiphenylamine, 2,7-diaminofluorene, 4,4'-dihydroxy-biphenylene, triphenylamine, 10-ethyl-4-phenothiazinecarboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-phenoxazinepropionic acid (POP), 10-(3-(4-methyl-1-piperazinyl)propyl)phenothlazine, 10-(2-pyrrolidinoethyl) phenothlazine, 10-methylphenoxazine, iminostilbene, 2-(p-aminophenyl)-6-methylbenzothiazole-7-sulfonic acid, N-benzylidene-4-biphenylamine, 5-amino-2-naphthalenesulfonic acid, 7-methoxy-2-naphthol, 4,4'-dihydroxybenzophenone, N-(4-(dimethylamino) benzylidene)-p-anisidine, 3-methyl-2-benzothiazolinone(4-(dimethylamino)benzylidene)hydrazone, 2-acethyl-10-methylphenothiazine, 10-(2-hydroxyethyl)pheriothiazine, 10-(2-hydroxyethyl)phenoxazine, 10-(3-hydroxypropyl) phenothiazine, 4,4'-dimethoxy-N-methyl-diphenylamine, vanillin azine, 4-hydroxybenzoic acid, L-tyrosine, syningate acids, ferulic acid, sinapic acid, chlorogenic acid, caffeic acid and esters thereof, acetosyringone, syringaldehyde, methyisyringate, syringic acid, ethylsyringate, propylsyringate, butylsyringate, hexylsyringate, octylsyringate and ethyl 3-(4-hydroxy-3,5-dimethoxyphenyl)acrylate, and combinations thereof.

8. The method of claim 1, wherein the amount is in the range of from 0.01–0.5%, calculated by weight of the dyeing composition.

9. The method of claim 1, wherein the chemical oxidizing agent is hydrogen peroxide.

10. The method of claim 1, wherein the chemical oxidizing agent is an oxidase acting upon a suitable substrate.

11. The method of claim 10, wherein the chemical oxidizing agent is glucose oxidase acting upon glucose.

12. A composition for treating hair comprising at least one laccase, one or more mediators, and at least one chemical oxidizing agent that produces hydrogen peroxide in an amount equivalent to 0.001–1% calculated by weight of the composition.

13. The composition of claim 12, wherein the chemical oxidizing agent is hydrogen peroxide or sodium perborate.

14. A coloring kit comprising, in separate components, (a) a chemical reducing agent, and (b) a dyeing composition comprising at least one laccase, one or more mediators, and at least one chemical oxidizing agent that produces hydrogen peroxide in an amount equivalent to 0.001–1% hydrogen peroxide calculated by weight of the dyeing composition.

* * * * *